US012539389B2

(12) United States Patent
Kugler et al.

(10) Patent No.: US 12,539,389 B2
(45) Date of Patent: Feb. 3, 2026

(54) CATHETERS AND RELATED DEVICES AND METHODS OF MANUFACTURE

(71) Applicant: Seigla Medical, Inc., Buffalo, MN (US)

(72) Inventors: Chad J. Kugler, Buffalo, MN (US); Ross A. Olson, Anoka, MN (US)

(73) Assignee: Seigla Medical, Inc., Buffalo, MN (US)

( * ) Notice: Subject to any disclaimer, the term of this patent is extended or adjusted under 35 U.S.C. 154(b) by 290 days.

(21) Appl. No.: 17/890,984

(22) Filed: Aug. 18, 2022

(65) Prior Publication Data

US 2023/0218858 A1 Jul. 13, 2023

Related U.S. Application Data

(63) Continuation-in-part of application No. 16/572,330, filed on Sep. 16, 2019, now Pat. No. 11,433,216.

(60) Provisional application No. 62/900,645, filed on Sep. 15, 2019, provisional application No. 62/899,929, (Continued)

(51) Int. Cl.
*A61M 25/00* (2006.01)

(52) U.S. Cl.
CPC ...... *A61M 25/0012* (2013.01); *A61M 25/005* (2013.01)

(58) Field of Classification Search
None
See application file for complete search history.

(56) References Cited

U.S. PATENT DOCUMENTS

| | | | |
|---|---|---|---|
| 4,478,898 | A | 10/1984 | Kato |
| 4,547,193 | A | 10/1985 | Rydell |
| 4,636,346 | A | 1/1987 | Gold et al. |

(Continued)

FOREIGN PATENT DOCUMENTS

| | | | |
|---|---|---|---|
| CN | 112494780 | A | 3/2021 |
| CN | 113384803 | A | 9/2021 |

(Continued)

OTHER PUBLICATIONS

Midgley, Measurements of the X-ray linear attenuation coefficient for low atomic No. materials at energies 32-66 and 140keV, Mar. 2005, Radiation Physics and Chemistry, vol. 72, Iss. 11, pp. 525-535 (Year: 2004).

(Continued)

*Primary Examiner* — Barbara J Musser
(74) *Attorney, Agent, or Firm* — Christensen, Fonder, Dardi & Herbert PLLC; John P. Fonder

(57) ABSTRACT

Methods for making medical devices and portions of medical devices (e.g., intravascular catheters, catheter shafts, and tubular guiding members) are provided. Example methods may include cutting a thin film extruded thermoplastic sheet into at least one ribbon and forming a first assembly by positioning the ribbon inside a shrink tube and urging the ribbon to assume a tubular shape in which the first ribbon defines a ribbon lumen. A second assembly may be formed by loading a lubricious inner tubular member over a mandrel and forming or placing a support structure over an outer surface of the lubricious inner tubular member. A third assembly may be formed by inserting the second assembly into the ribbon lumen defined by the ribbon of the first assembly. The third assembly may be heated to a process temperature, and the shrink tube may be removed.

10 Claims, 20 Drawing Sheets

Related U.S. Application Data filed on Sep. 13, 2019, provisional application No. 62/732,282, filed on Sep. 17, 2018.

(56) References Cited

U.S. PATENT DOCUMENTS

| | | | |
|---|---|---|---|
| 5,047,045 | A | 9/1991 | Arney et al. |
| 5,120,323 | A | 6/1992 | Shockey et al. |
| 5,217,440 | A | 6/1993 | Frassica |
| 5,400,785 | A | 3/1995 | Crowley |
| 5,439,445 | A | 8/1995 | Kontos |
| 5,540,707 | A | 7/1996 | Ressemann et al. |
| 5,569,221 | A | 10/1996 | Houser et al. |
| 5,628,787 | A | 5/1997 | Mayer |
| 5,667,499 | A | 9/1997 | Welch et al. |
| 5,695,468 | A | 12/1997 | Lafontaine et al. |
| 5,785,685 | A | 7/1998 | Kugler et al. |
| 5,836,868 | A | 11/1998 | Ressemann et al. |
| 5,897,567 | A | 4/1999 | Ressemann et al. |
| 5,911,715 | A | 6/1999 | Berg et al. |
| 5,980,486 | A | 11/1999 | Enger |
| 6,092,526 | A | 7/2000 | LaFontaine et al. |
| 6,093,177 | A | 7/2000 | Javier, Jr. et al. |
| 6,129,756 | A | 10/2000 | Kugler et al. |
| 6,183,443 | B1 | 2/2001 | Kratoska et al. |
| 6,217,566 | B1 | 4/2001 | Ju et al. |
| 6,273,909 | B1 | 8/2001 | Kugler et al. |
| 6,280,466 | B1 | 8/2001 | Kugler et al. |
| 6,443,158 | B1 | 9/2002 | LaFontaine et al. |
| 6,508,806 | B1 | 1/2003 | Hoste |
| 6,517,572 | B2 | 2/2003 | Kugler et al. |
| 6,638,245 | B2 | 10/2003 | Miller et al. |
| 6,652,572 | B2 | 11/2003 | Kugler et al. |
| 6,790,222 | B2 | 9/2004 | Kugler et al. |
| 6,884,260 | B2 | 4/2005 | Kugler et al. |
| 6,939,371 | B2 | 9/2005 | Kugler et al. |
| 6,979,319 | B2 | 12/2005 | Manning et al. |
| 6,991,617 | B2 | 1/2006 | Hektner et al. |
| 7,101,361 | B2 | 9/2006 | Gardeski |
| 7,112,217 | B1 | 9/2006 | Kugler et al. |
| 7,306,585 | B2 | 12/2007 | Ross |
| 7,316,678 | B2 | 1/2008 | Nash et al. |
| 7,445,010 | B2 | 11/2008 | Kugler et al. |
| 7,497,822 | B1 | 3/2009 | Kugler et al. |
| 7,553,387 | B2 | 6/2009 | Leeflang et al. |
| 7,556,642 | B2 | 7/2009 | Trotta |
| 7,604,612 | B2 | 10/2009 | Ressemann et al. |
| 7,644,714 | B2 | 1/2010 | Atkinson et al. |
| 7,674,411 | B2 | 3/2010 | Berg et al. |
| 7,674,421 | B2 | 3/2010 | Ross |
| 7,695,427 | B2 | 4/2010 | Kugler et al. |
| 7,717,899 | B2 | 5/2010 | Bowe et al. |
| 7,736,355 | B2 | 6/2010 | Itou et al. |
| 7,762,984 | B2 | 7/2010 | Kumoyama et al. |
| 7,771,369 | B2 | 8/2010 | Griffin et al. |
| 7,896,825 | B2 | 3/2011 | Atkinson et al. |
| 7,918,870 | B2 | 4/2011 | Kugler et al. |
| 7,938,819 | B2 | 5/2011 | Kugler et al. |
| 8,025,655 | B2 | 9/2011 | Kugler et al. |
| 8,048,032 | B2 | 11/2011 | Root et al. |
| 8,083,727 | B2 | 12/2011 | Kugler et al. |
| 8,142,413 | B2 | 3/2012 | Root et al. |
| 8,172,863 | B2 | 5/2012 | Robinson et al. |
| 8,187,164 | B2 | 5/2012 | Kugler et al. |
| 8,202,246 | B2 | 6/2012 | Kugler et al. |
| 8,292,827 | B2 | 10/2012 | Musbach et al. |
| 8,292,850 | B2 | 10/2012 | Root et al. |
| 8,323,261 | B2 | 12/2012 | Kugler et al. |
| 8,337,425 | B2 | 12/2012 | Olson et al. |
| 8,496,679 | B2 | 7/2013 | Robinson et al. |
| 8,512,310 | B2 | 8/2013 | Kugler et al. |
| 8,632,556 | B2 | 1/2014 | Jacobs et al. |
| 8,636,712 | B2 | 1/2014 | Kugler et al. |
| 8,709,028 | B2 | 4/2014 | Robinson et al. |
| 8,753,312 | B2 | 6/2014 | Bowe et al. |
| RE45,380 | E | 2/2015 | Root et al. |
| 8,961,494 | B2 | 2/2015 | Kugler et al. |
| 8,996,095 | B2 | 3/2015 | Anderson et al. |
| 9,005,225 | B2 | 4/2015 | Robinson et al. |
| 9,060,802 | B2 | 6/2015 | Kugler et al. |
| 9,067,042 | B2 | 6/2015 | Gardeski et al. |
| RE45,760 | E | 10/2015 | Root et al. |
| RE45,776 | E | 10/2015 | Root et al. |
| 9,149,604 | B2 | 10/2015 | Nishide et al. |
| 9,199,064 | B2 | 12/2015 | Morero |
| 9,237,897 | B2 | 1/2016 | Kugler et al. |
| 9,308,019 | B2 | 4/2016 | Kugler et al. |
| 9,351,747 | B2 | 5/2016 | Kugler et al. |
| 9,352,123 | B2 | 5/2016 | Zhou et al. |
| RE46,116 | E | 8/2016 | Root et al. |
| 9,468,494 | B2 * | 10/2016 | O'Sullivan ............. B29C 33/52 |
| 9,486,611 | B2 | 11/2016 | Petersen et al. |
| 9,656,042 | B2 | 5/2017 | Takagi et al. |
| 9,717,889 | B2 | 8/2017 | Kugler et al. |
| 9,764,118 | B2 | 9/2017 | Anderson et al. |
| 9,782,561 | B2 | 10/2017 | Kugler et al. |
| 9,788,855 | B2 | 10/2017 | Kugler et al. |
| 9,801,746 | B2 | 10/2017 | Ogawa et al. |
| 9,872,685 | B2 | 1/2018 | Kugler et al. |
| 9,878,128 | B2 | 1/2018 | Kugler et al. |
| 9,913,961 | B2 | 3/2018 | Cajamarca et al. |
| 9,931,026 | B2 | 4/2018 | Ha et al. |
| 9,943,314 | B2 | 4/2018 | Kugler et al. |
| 9,968,763 | B2 | 5/2018 | Root et al. |
| 9,993,613 | B2 | 6/2018 | Wang et al. |
| 10,016,188 | B2 | 7/2018 | Jacobs et al. |
| 10,124,147 | B2 | 11/2018 | Anderson et al. |
| 10,124,148 | B2 | 11/2018 | Falk et al. |
| 10,143,487 | B2 | 12/2018 | Kugler et al. |
| 10,159,821 | B2 | 12/2018 | Root et al. |
| 10,166,035 | B2 | 1/2019 | Kugler et al. |
| 10,173,052 | B2 | 1/2019 | Daniels et al. |
| 10,192,230 | B2 | 1/2019 | Look et al. |
| 10,245,050 | B2 | 4/2019 | Kugler |
| RE47,379 | E | 5/2019 | Root et al. |
| 10,315,010 | B2 | 6/2019 | Kugler et al. |
| 10,342,569 | B2 | 7/2019 | Kugler et al. |
| 10,390,806 | B2 | 8/2019 | Lee et al. |
| 10,390,849 | B2 | 8/2019 | Kugler et al. |
| 10,391,305 | B2 | 8/2019 | Asleson et al. |
| 10,398,440 | B2 | 9/2019 | Kugler et al. |
| 10,448,940 | B2 | 10/2019 | Jacobs et al. |
| 10,478,546 | B2 | 11/2019 | Slager et al. |
| 10,485,956 | B2 | 11/2019 | O'Donovan |
| 10,537,709 | B2 | 1/2020 | Fuller et al. |
| 10,569,050 | B1 | 2/2020 | Heesch |
| 10,617,847 | B2 | 4/2020 | Cottone et al. |
| 10,639,462 | B2 | 5/2020 | Matlock et al. |
| 10,682,494 | B2 | 6/2020 | Fuller et al. |
| 10,688,277 | B2 | 6/2020 | O'Connell et al. |
| 10,729,884 | B2 | 8/2020 | Connolly et al. |
| 10,751,514 | B2 | 8/2020 | Brenizer et al. |
| 10,780,247 | B2 | 9/2020 | Norman et al. |
| 10,946,177 | B2 | 3/2021 | Peterson et al. |
| 10,953,197 | B2 | 3/2021 | Brenizer et al. |
| 11,000,676 | B2 | 5/2021 | Holzer |
| 11,027,093 | B2 | 6/2021 | Haldis et al. |
| 11,197,977 | B2 | 12/2021 | Mullins et al. |
| 11,433,216 | B2 * | 9/2022 | Kugler ................ B29C 65/4815 |
| 11,547,835 | B2 * | 1/2023 | Kugler ................ A61M 25/005 |
| 2001/0016702 | A1 | 8/2001 | Benjamin |
| 2001/0053931 | A1 | 12/2001 | Hess et al. |
| 2002/0143360 | A1 | 10/2002 | Douk et al. |
| 2003/0093105 | A1 | 5/2003 | Huffmaster |
| 2003/0125709 | A1 | 7/2003 | Eidenschink |
| 2004/0010280 | A1 | 1/2004 | Adams et al. |
| 2004/0116832 | A1 | 6/2004 | Friedrich et al. |
| 2004/0122360 | A1 | 6/2004 | Waldhauser et al. |
| 2005/0015073 | A1 | 1/2005 | Kataishi et al. |
| 2005/0027345 | A1 | 2/2005 | Horan et al. |
| 2005/0119616 | A1 | 6/2005 | Goodin et al. |
| 2007/0260219 | A1 | 11/2007 | Root et al. |
| 2008/0065049 | A1 | 3/2008 | Harris et al. |
| 2008/0125752 | A1 | 5/2008 | Gunderson et al. |
| 2009/0024110 | A1 | 1/2009 | Heideman et al. |

(56) References Cited

U.S. PATENT DOCUMENTS

| | | | | |
|---|---|---|---|---|
| 2009/0196178 | A1 | 8/2009 | Stewart et al. | |
| 2009/0198178 | A1 | 8/2009 | Gurm | |
| 2009/0240235 | A1 | 9/2009 | Murata | |
| 2010/0324567 | A1 | 12/2010 | Root et al. | |
| 2011/0208164 | A1 | 8/2011 | Pal | |
| 2012/0041411 | A1 | 2/2012 | Horton et al. | |
| 2012/0165756 | A1 | 6/2012 | Root et al. | |
| 2014/0012281 | A1 | 1/2014 | Wang et al. | |
| 2014/0018773 | A1 | 1/2014 | Wang et al. | |
| 2014/0025043 | A1 | 1/2014 | Wang et al. | |
| 2014/0039461 | A1 | 2/2014 | Anderson et al. | |
| 2014/0052097 | A1 | 2/2014 | Petersen et al. | |
| 2014/0081243 | A1 | 3/2014 | Zhou et al. | |
| 2014/0249508 | A1 | 9/2014 | Wang et al. | |
| 2015/0151090 | A1 | 6/2015 | Sutton et al. | |
| 2015/0246209 | A1 | 9/2015 | Holzer | |
| 2015/0320971 | A1 | 11/2015 | Leeflang et al. | |
| 2016/0101261 | A1 | 4/2016 | Kugler et al. | |
| 2016/0114126 | A1 | 4/2016 | Heideman et al. | |
| 2016/0121080 | A1* | 5/2016 | Cottone ............ | A61M 25/0069 604/528 |
| 2016/0136394 | A1 | 5/2016 | Kobayashi et al. | |
| 2016/0175569 | A1 | 6/2016 | Heuser | |
| 2016/0346502 | A1 | 12/2016 | Fuller et al. | |
| 2016/0346515 | A1 | 12/2016 | Buller et al. | |
| 2017/0028170 | A1 | 2/2017 | Ho | |
| 2017/0087339 | A1 | 3/2017 | Taber | |
| 2017/0252043 | A1 | 9/2017 | Fuller et al. | |
| 2017/0296783 | A1 | 10/2017 | Connolly et al. | |
| 2017/0354800 | A1 | 12/2017 | O'Donovan | |
| 2018/0028177 | A1 | 2/2018 | Van Oepen et al. | |
| 2018/0104445 | A1 | 4/2018 | Fuller et al. | |
| 2018/0161547 | A1 | 6/2018 | Brenizer et al. | |
| 2018/0228502 | A1 | 8/2018 | Shaffer et al. | |
| 2019/0030283 | A2 | 1/2019 | Cottone | |
| 2019/0117938 | A1 | 4/2019 | Norman et al. | |
| 2019/0151607 | A9 | 5/2019 | O'Connell et al. | |
| 2019/0160259 | A1 | 5/2019 | Cottone et al. | |
| 2019/0247619 | A1 | 8/2019 | Brenizer et al. | |
| 2019/0255297 | A1 | 8/2019 | Fischell et al. | |
| 2019/0255299 | A1 | 8/2019 | Fischell et al. | |
| 2019/0358434 | A1 | 11/2019 | Fuller et al. | |
| 2019/0366049 | A1 | 12/2019 | Hannon et al. | |
| 2020/0155732 | A1 | 5/2020 | Rangwala et al. | |
| 2020/0353205 | A1 | 11/2020 | Kelly et al. | |
| 2020/0398028 | A1 | 12/2020 | Cottone | |
| 2021/0008342 | A1 | 1/2021 | Buller et al. | |
| 2021/0038863 | A1 | 2/2021 | Cooney et al. | |
| 2021/0046289 | A1 | 2/2021 | McEvoy et al. | |
| 2022/0040454 | A1 | 2/2022 | Hamm et al. | |
| 2022/0096795 | A1 | 3/2022 | Brenizer | |
| 2022/0176075 | A1 | 6/2022 | McDermott et al. | |

FOREIGN PATENT DOCUMENTS

| | | | |
|---|---|---|---|
| CN | 114082075 | A | 2/2022 |
| DE | 10 2005 023 414 | B3 | 11/2006 |
| WO | WO2001010492 | A1 | 2/2001 |
| WO | WO2005004969 | A1 | 1/2005 |
| WO | WO2006020044 | A1 | 2/2006 |
| WO | WO2006039392 | A2 | 4/2006 |
| WO | WO2009085486 | A1 | 7/2009 |
| WO | WO2013070758 | | 5/2013 |
| WO | WO2013185148 | | 12/2013 |
| WO | WO2014043694 | | 3/2014 |
| WO | WO2020061076 | A1 | 3/2020 |
| WO | WO2020061088 | A1 | 3/2020 |

OTHER PUBLICATIONS

Takahashi et al., New Method to Increase a Backup Support of a 6 French Guiding Coronary Catheter, Catheterization and Cardiovascular Interventions 63:452-456 (2004).

International Search Report for Application No. PCT/US2019/051554, mailed Dec. 4, 2019, 2 pages.

International Search Report for Application No. PCT/US2019/51554, mailed Dec. 4, 2019, 2 pages.

International Search Report for Application No. PCT/US2019/051569, mailed Nov. 20, 2019, 2 pages.

Saeko Takahashi, et al., New Method to Increase a Backup Support of a 6 French Guiding Coronary Catheter, Catheterization and Cardiovascular Interventions 63:452-456 (2004).

* cited by examiner

CATHETERS AND RELATED DEVICES AND METHODS OF MANUFACTURE

CROSS-REFERENCE TO RELATED APPLICATIONS

The present application is a continuation-in-part of U.S. application Ser. No. 16/572,330, filed Sep. 16, 2019 now U.S. Pat. No. 11,433,1216, which claims the benefit of U.S. Provisional Application No. 62/900,645, filed Sep. 15, 2019, U.S. Provisional Application No. 62/899,929, filed Sep. 13, 2019, and U.S. Provisional Application No. 62/732,282, filed Sep. 17, 2018, the disclosures of which are incorporated by reference herein. The present application is also related to U.S. application Ser. No. 17/584,627 filed Jan. 26, 2022, which is a continuation-in-part of U.S. application Ser. No. 17/508,459 filed Oct. 22, 2021, which is also a continuation-in-part of U.S. application Ser. No. 16/572,330, and which also claims the benefit of U.S. Provisional Application No. 62/900,645, U.S. Provisional Application No. 62/899,929, and U.S. Provisional Application No. 62/732,282.

FIELD

The present disclosure relates to intraluminal catheters such as intravascular coronary, peripheral and neuro catheters, intrabronchial catheters and other catheters used in small caliber anatomy.

BACKGROUND

Catheters are used in a wide variety of medical procedures. In some challenging applications, the catheter must navigate a long, narrow and tortuous path to get from the access site to the treatment site. Thus, catheter designs often balance therapeutic or diagnostic function with flexibility, pushability and profile, especially in small caliber anatomy. In such applications, it may be desirable to have as small of a cross-sectional profile as possible, and/or as large of a working lumen as possible.

Generally speaking, at least a portion of the catheter is formed by assembling polymeric tubes, often with multiple polymeric layers and metallic reinforcement such as a coil or braid. The polymeric tubes are generally formed by extrusion. The profile of the catheter is substantially influenced by the wall thickness of the tubular extrusion. However, commonly used polymeric extrusions are limited in terms of how thin the wall thickness can be made.

In general, with thermoplastic extrusions of any type, the extrusion process is generally governed by the control of polymer volume flow. Tight mechanical control of the extruder lead screw (pump) provides tight control of final dimensions of any extruded part. The miniature nature of medical tubing extrusions presents a polymer volume control challenge. Slight variations in lead screw performance can result in meaningful differences in polymer volume flow and variations in the ultimate dimensions of the extruded part. A tubular wall thickness of 0.0015"+/−0.0005" is generally accepted as the industry standard lower limit for thermoplastic medical tubing extrusion. At that dimension, tubular extrusion is a low volume process.

Thus, it would be desirable to have a wall-thicknesses less than 0.0015" and tolerances tighter than 0.0005" (or 33%) to enable different catheter constructions to achieve the lowest profile possible, largest working lumen possible and enable better performing catheters for access to smaller caliber anatomy.

SUMMARY

In an example embodiment, the present disclosure provides new catheter constructions involving the use of thin film extrusions. Generally speaking, thin (flat) film extrusions may be made substantially thinner than tubular extrusions with tighter manufacturing tolerances. As mentioned above, tubular extrusion is a low volume process. By contrast, thin sheet of film is a higher volume process, so thinner walls may be achieved. In thin film extrusions, the extrusion is thin and wide. As compared to a small tube the polymer volume flow is high and variations in pump performance are less meaningful. The tooling for thin film can be adjusted during the extrusion process vs. hard tooling for tube extrusion. This allows adjustment of the tooling during a run and ensures dimensional requirements are met. The dwell time within the extruder is an important factor. If flow is too low, the polymer degrades. Ultra-thin small tubes do not have enough flow volume.

Specifically, thin film extrusion is higher polymer volume flow and less sensitive to extruder pump performance variation as compared to tube extrusion. By way of example, the polymer volume of a thin film extrusion that is 6.0" wide and 0.0015" thick is volumetrically equivalent to approximately 27 extruded tubes with an internal diameter of 0.070" of equivalent wall thickness. This increased extrusion flow volume makes thin film extrusion less sensitive to processing variations (averaging the variations over the entire width) and enables thinner extrusions without creating low flow, a long heat history, and polymer degradation. In addition, the thin film extrusion die is mechanically simple and adjustable enabling titration during an extrusion run to achieve accurate dimensions.

Using thin film extrusion, tubes with a wall thickness less than 0.0015" may be made using the techniques described herein. In addition to thinner walls, tighter dimensional tolerances can be achieved by thin film extrusion because of the aforementioned variables. For example, tubes may be made with thin film extrusion with a wall thickness less than 0.0015", preferably 0.0010", 0.0075", 0.0005" or even 0.0003", with corresponding tolerances of ±0.0002", 0.00013", 0.0001", and less than 0.0001".

The example embodiments described herein may be used alone or in combination to achieve the desired result. In each case, the result may be a catheter with a lower profile and/or larger working lumen with better performance. The catheter may comprise a coronary, peripheral and neuro guide catheter, diagnostic catheter, aspiration catheter, microcatheter, balloon catheter, stent delivery catheter or the like.

In one example embodiment, a catheter comprises an elongate tubular shaft that includes a thin film polymeric layer with two opposing long edges. The thin film may have a thickness of less than 0.0015" and a tolerance of less than 0.0005" (or 33%). Preferably, the thin film thickness may be less than 0.0010", 0.00075" or even 0.00050" depending on the application. The thin film may have a length that is greater than its width to define a thin film elongate ribbon. The width of the ribbon may approximate the circumference of the tubular shaft. The thin film may extend around the longitudinal axis to define a tubular shape with the edges abutting each other to form a joint. The joint may be linear (e.g., straight) or non-linear (e.g., helical) and may be continuous or discontinuous. The tubular-shaped thin film layer may have a uniform wall thickness around the circumference, and the uniform wall thickness may extend across the joint.

The elongate shaft may further include a reinforcement layer disposed over an inner liner with the thin film layer disposed over the reinforcement layer. The reinforcement layer may comprise metal such as a braid or coil.

The thin film polymeric layer may comprise a first thin film layer and a second thin film layer, wherein the first thin film layer is connected to the second thin film layer end-to-end to define a circumferential joint. The circumferential joint may orthogonal or at an acute angle to the longitudinal axis. The first thin film layer may comprise a material that is different than the material of the second thin film layer. The materials may be different in terms of composition, dimension or other characteristic such as hardness, flexibility color, thickness or radiopacity, for example. One or more layers of thin film may be employed, with each layer comprising the same, similar or different material as described above.

In another example embodiment, a method of making catheter or a portion thereof is described. The method may comprise providing a thin film polymeric sheet having a thickness of less than 0.0015", for example, and two opposing long edges. The thin film may be rolled such that the two opposing long edges form a gap. Heat and force may be applied along the edges such that the gap closes, the edges abut each other, and a longitudinal joint is formed. The heat and force may be removed to result in a thin film tube.

BRIEF DESCRIPTION OF THE FIGURES

The drawings, along with the detailed description, serve to illustrate various embodiments, concepts and principles of the present disclosure. A brief description of the drawings, which are not necessarily to scale, follows.

While embodiments and aspects of the present disclosure are amenable to various modifications and alternative forms, specifics thereof have been shown and described by way of example, not limitation.

DETAILED DESCRIPTION

Figure 1:
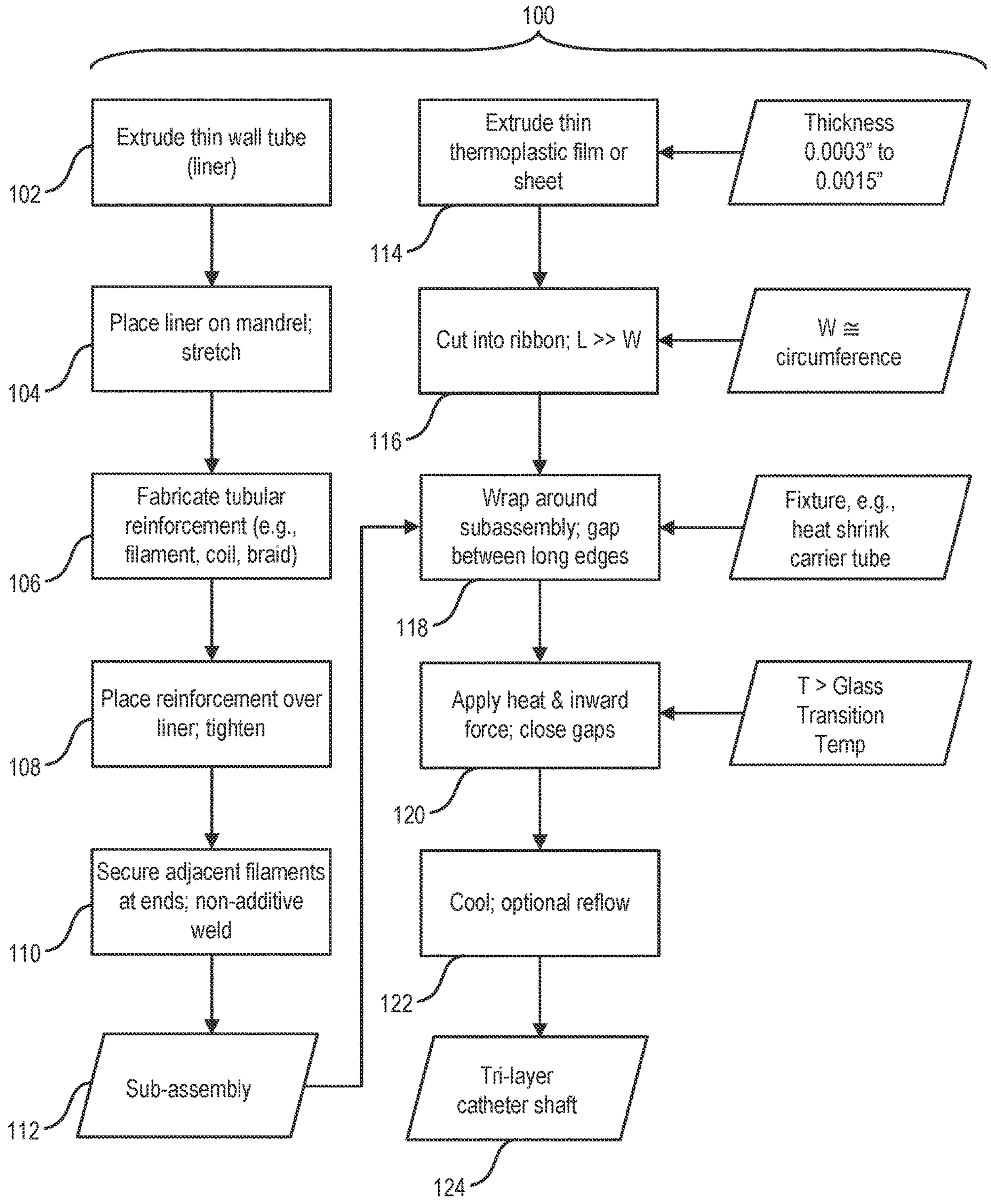
FIG. 1 is a schematic flow chart of a manufacturing method according to an embodiment of the present disclosure for making a catheter or portion thereof with a thin film sheet.

FIG. 1 is a schematic flow chart of an example manufacturing process 100 using thin film to make a portion of a catheter. The manufacturing method 100 is explained in general steps with reference to FIG. 1, and variations are described elsewhere herein. The manufacturing process 100 may be applied to a wide variety of catheters, some of which are described herein. In the example shown in FIG. 1, the manufacturing process 100 is described with reference to a tri-layer catheter construction, but the thin film technique may be applied to other catheter constructions. When describing the manufacturing method 100, reference is made to FIGS. 2A-2L to show the components being assembled.

For a tri-layer construction, a liner and reinforcement subassembly may be manufactured, onto which a thin film may be applied. To make the liner and reinforcement subassembly, a thin-walled tube (inner or liner) 202 may be extruded 102 using conventional tubular extrusion techniques. Alternatively, the liner 202 may be formed from thin film ribbon as described herein. It may be desirable that the liner 202 be lubricious, in which case the liner 202 may be made of PTFE or HDPE, for example. Thin-walled PTFE tubing is available from a variety of vendors including Zeus of Orangeburg, SC, USA or Junkosha of Tokyo, Japan. For intravascular applications over a 0.014" diameter guidewire, the wall thickness of the liner may be 0.0015" with an inside diameter of about 0.016", for example. The length of the liner 202 may approximate the overall length of the catheter or a portion thereof, ranging from 10 cm to 175 cm, for example.

Figure 2A:
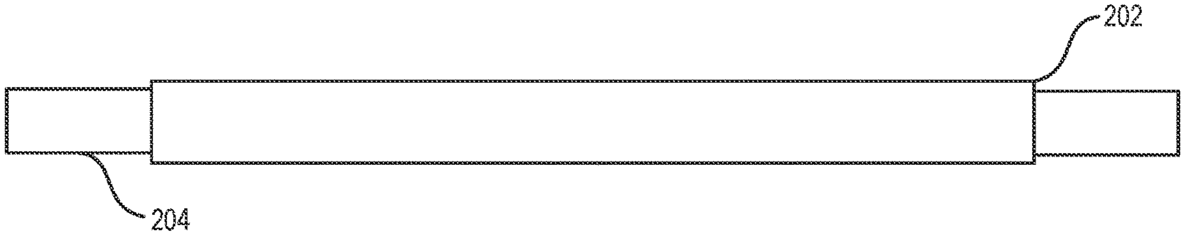
FIGS. 2A-2L are schematic illustrations of parts, assemblies and subassemblies of the manufacturing method shown in FIG. 1.

To facilitate construction, the liner 202 may be placed 104 on a mandrel 204 as shown in FIG. 2A. Optionally, the mandrel 204 may comprise annealed stainless-steel such that it may be subsequently removed by stretching causing it to become longer and thinner to ease removal. Also optionally, the liner 202 may be stretched 104 on the mandrel 204 to achieve a thinner wall thickness.

Figure 2B:
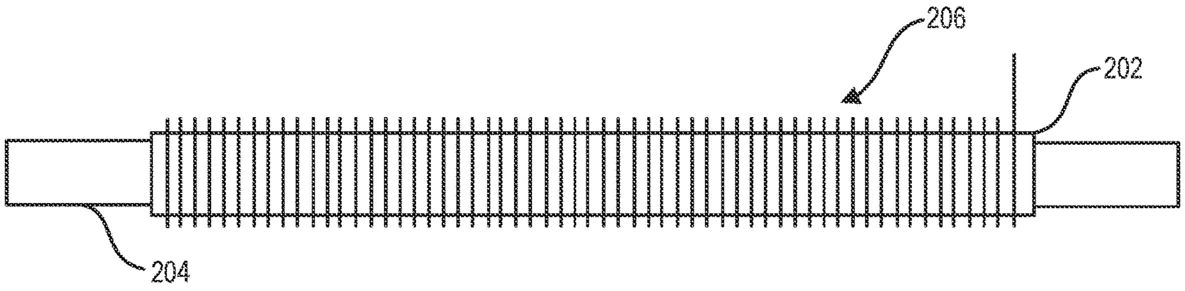

A reinforcement layer 206 may be fabricated 106 as a separate component and placed 108 on the liner 202 or fabricated 106 directly on the liner 102. For example, the reinforcement layer 206 may comprise braided stainless-steel wire fabricated by conventional means as a separate component. Alternatively, the reinforcement layer 206 may comprise a coiled stainless-steel wire wound directly on the liner 202. By way of example, not limitation, FIG. 2B show a coil 206 being wound directly on the liner 202. The reinforcement layer 206 may be monofilament or multifilament with varying pic count or pitch as desired.

Figure 2C:
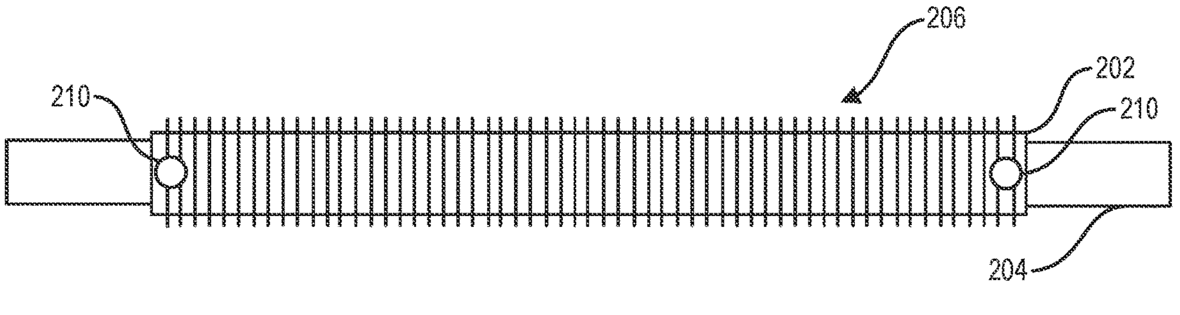

The reinforcement layer 202 may be tightened 108 (if not already) and the ends may be secured 110 to avoid unwinding, unraveling or otherwise becoming loose. Securing 110 the ends of the reinforcement layer 206 may be accomplished by additive means such as by using a heat-shrink sleeve or an adhesive. Alternatively, the ends may be secured 110 by a non-additive means such as by welding 210 adjacent filaments or windings of the reinforcement layer 206 as shown in FIG. 2C. An example of a suitable welder is a 100W Ytterbium fiber laser with the following settings: 50-100% (75% nominal) power; 0.1-0.5 ms (0.3 ms nominal) pulse width; 1-10 mm/min (3 mm/min nominal) feed rate; 1-10 Hz (3 Hz nominal) frequency; and 0.0025-0.0050"

(0.0045" nominal) spot size. The laser may be aimed at the seam between adjacent windings such that heat from the laser causes metal to flow between adjacent windings to form a weld joint upon cooling. With the reinforcement layer 206 secured tightly on the liner 202, the subassembly is complete 112.

An outer thin film layer may be disposed over the subassembly 112 by initially extruding 114 a flat and thin thermoplastic film or sheet 220. As mentioned previously, it is possible to achieve a thinner wall with a flat film or sheet extrusion than with a tube extrusion for the reasons explained previously. For example, whereas thermoplastic tube extrusions typically reach their lower limit of wall thickness around 0.0015", thin film extrusions can attain a wall thickness well below 0.0015", down to 0.0003", for example. Any wall thickness (T) may be selected for the thin film sheet 220, but wall thicknesses of less than 0.0015", and preferably 0.001" or less may be used to achieve a lower profile. Thin film sheet extrusions are available from multiple vendors such as Peak Nano of Valley View, OH, or Polyzen, Inc. of Apex, NC. Examples of a suitable thin film sheet material include thermoplastic elastomers (TPE) such as polyether block amide (e.g., PEBAX, VESTAMID) or polyamides generally (aka, nylons), polyethylenes (e.g., LDPE, HDPE), etc.

Figure 2D:
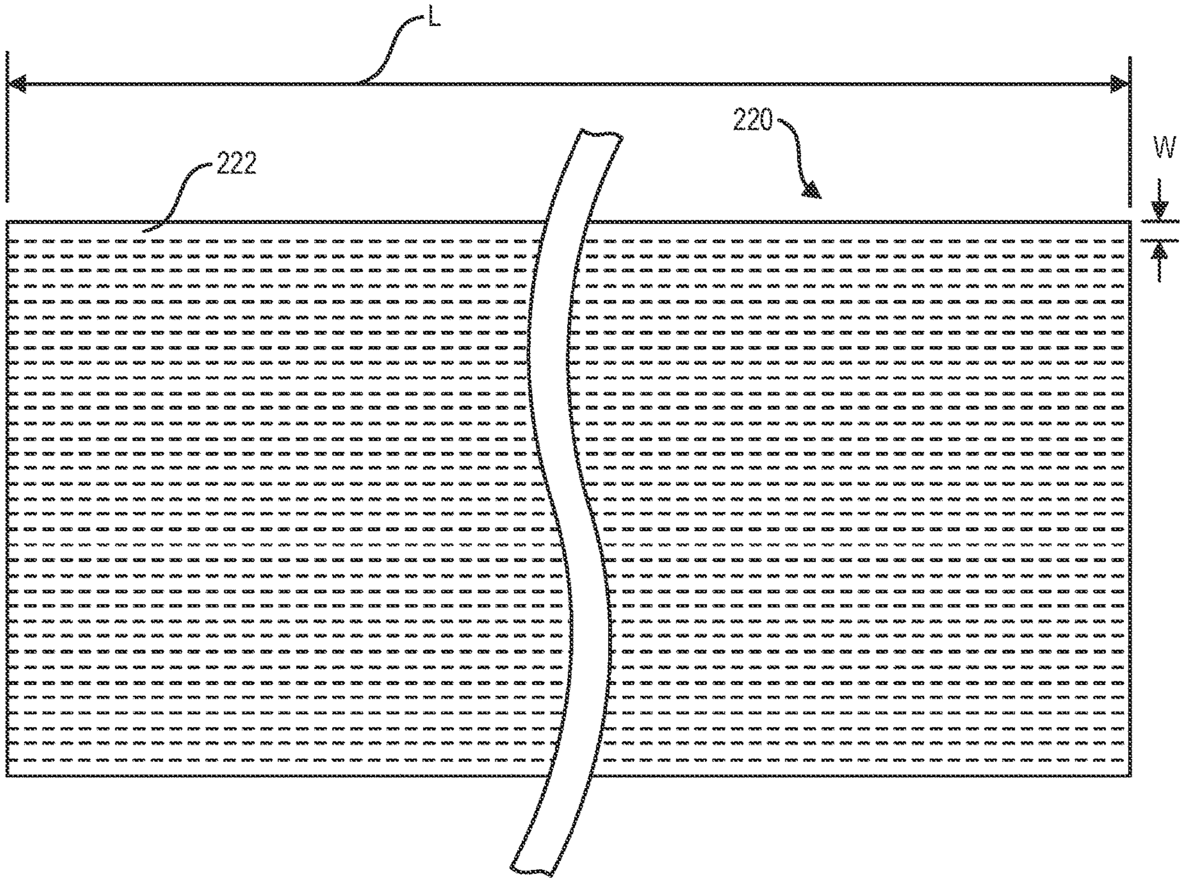
Figure 2E:
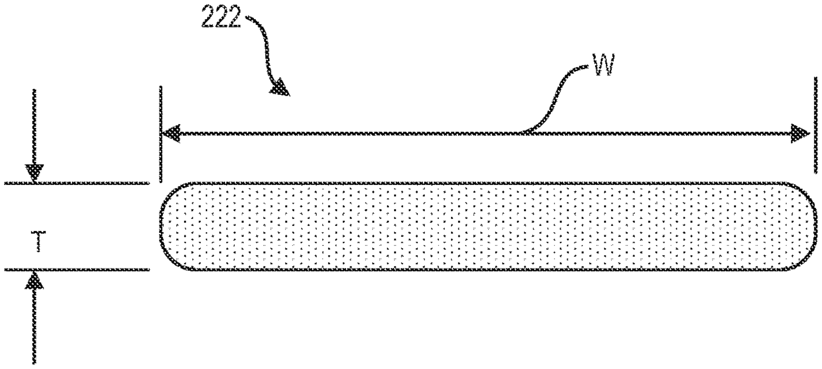

As shown in FIGS. 2D and 2E, the thin film sheet 220 may be cut 116 into ribbons 222 wherein the width (W) is substantially greater than the length (L), for example, and wherein the width and length of the ribbons 222 correspond to the outside circumference and length, respectively, of the subassembly 112. The ribbons 222 may be cut from the sheet 220 by shearing or laser cutting, for example. For laser cutting, the sheet 220 may be placed in a masking fixture with voids defining where the laser may pass to cut the sheet 220. The laser cuts may be made in two passes, one on each side of the sheet 220 passing partway through to provide a smooth cut free of burrs or flash. The result is a plurality of ribbons 222, each having a precise wall thickness (T), length (L) and width (W). An example of a suitable laser is a 100W Ytterbium fiber laser with the following settings: 50-100% (80% nominal) power; and 0.3-1.0 ms (0.55 ms nominal) pulse width. The masking fixture may be made from a laser cut or milled metal plate such as stainless-steel.

Figure 2F:
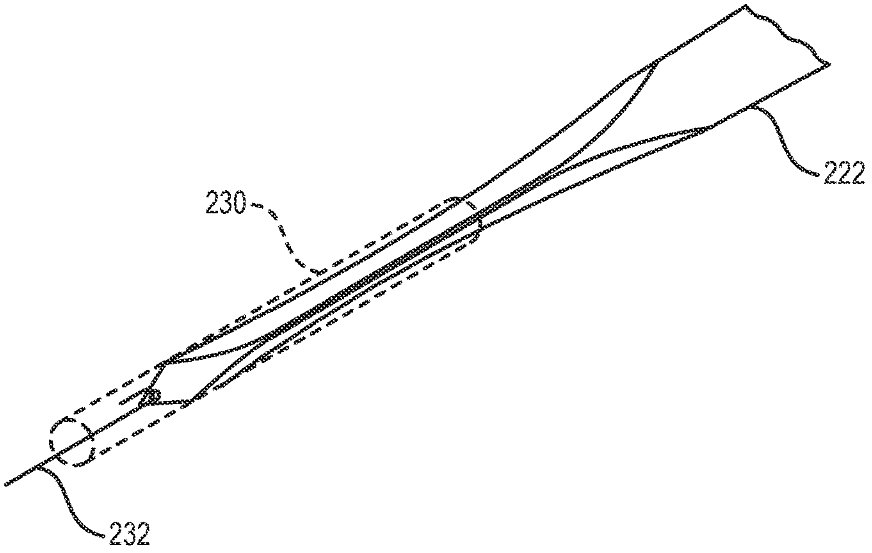
Figure 2G:
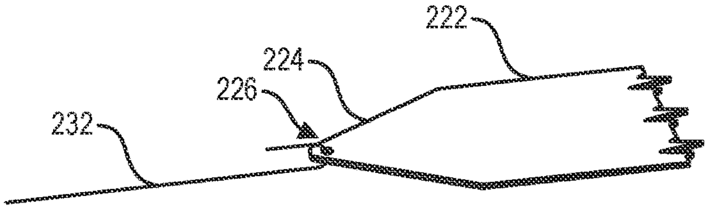
Figure 2H:
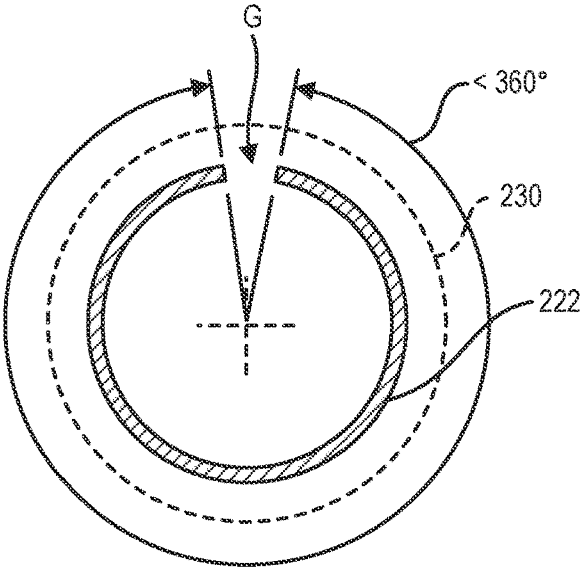

A ribbon 222 may then be wrapped 118 around the subassembly 112, wherein the width of the ribbon 222 spans the circumference of the subassembly 112 and the long edges along the length of the ribbon 222 extend along the length of the subassembly 112 to define a longitudinal gap (G) therebetween as shown in FIG. 2H. To facilitate wrapping of the ribbon 222 around the subassembly 112, a fixture may be utilized. For example, the ribbon 222 may be preloaded in a carrier tube 230, such as a heat-shrink tube as shown in FIG. 2F. The ribbon 222 may include a tapered end 224 and hole 226 formed at one end thereof during the cutting process to facilitate pulling (or pushing) the ribbon 222 into the carrier tube 230 using a pulling (or pushing) device 232 releasably connected to the ribbon 222 via hole 226 as shown in FIG. 2G. As the ribbon 222 enters the carrier tube 230, the tapered end 224 engages the circular end of the carrier tube 230 causing the ribbon 222 to roll as shown in FIG. 2F.

Figure 2I:
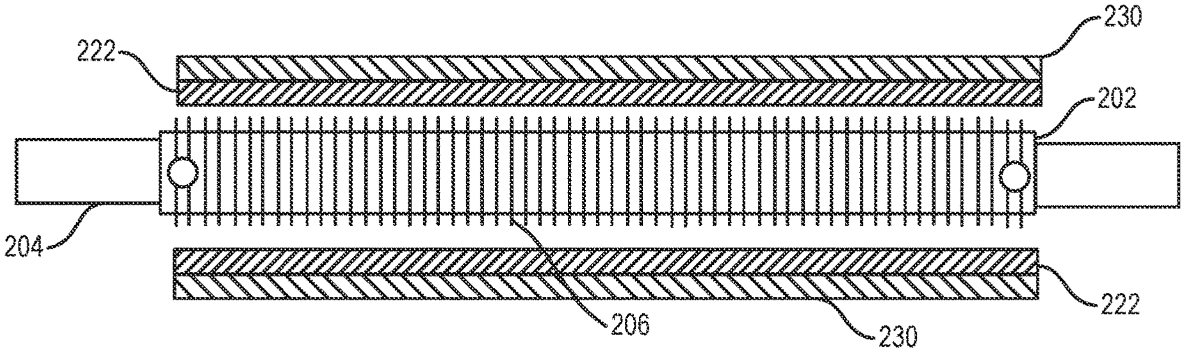

The carrier tube 230, with the ribbon 222 rolled therein, may be slid onto the subassembly 112 such that the ribbon 222 is essentially wrapped 118 around the subassembly 112, with a linear gap (G) between the long edges of the ribbon 222, and an annular space between the inner surface of the ribbon 222 and the outer surface of the subassembly 112 as shown in FIG. 2I. The ribbon 222 may be wrapped in a linear fashion (straight or longitudinal) or a nonlinear fashion (e.g., helical or spiral). Optionally, rather than defining a gap, the long edges may abut each other or overlap.

Figure 2J:
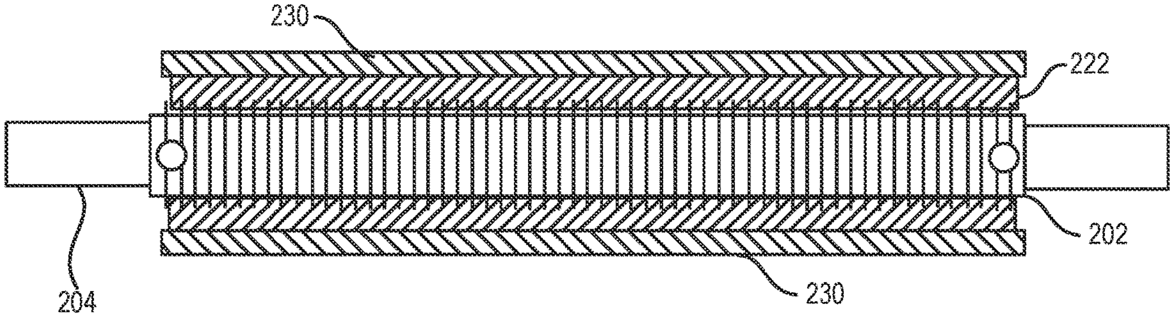

The linear gap (G) and the annular space may be closed by the application 120 of heat and inward force, thus forming a joint. Sufficient heat may be applied to cause the ribbon 222 to be at a temperature above the glass transition temperature of the ribbon 222 material. Thermal energy may be applied by convectively (e.g., hot air gun), conductively (e.g., drawing through a heated die or hot jaws) or radiantly (e.g., laser or heat lamp), for example. The inward force may be applied by compression outside the ribbon 222 or vacuum inside the ribbon 222. In the illustrated example, heat and compression are applied 120 to cause the heat-shrink carrier tube 230 to compress and mold the ribbon 222 onto the subassembly, thus closing the linear gap (G) and the annular space, and creating a bond between the ribbon 222 and subassembly 112 as shown in FIG. 2J. When the gap (G) is closed, a longitudinal joint or seam may be formed, although perhaps not visible, wherein the longitudinal edges of the ribbon abut each other and are bonded and the polymeric material flows together to form an outer thin film layer. It may be preferable to have the longitudinal edges abut each other, as opposed to overlapping each other, to minimize profile. If visible, the longitudinal joint or seam may serve to inform the user of the rotational position of the catheter as it is torqued during navigation, for example.

Figure 2K:
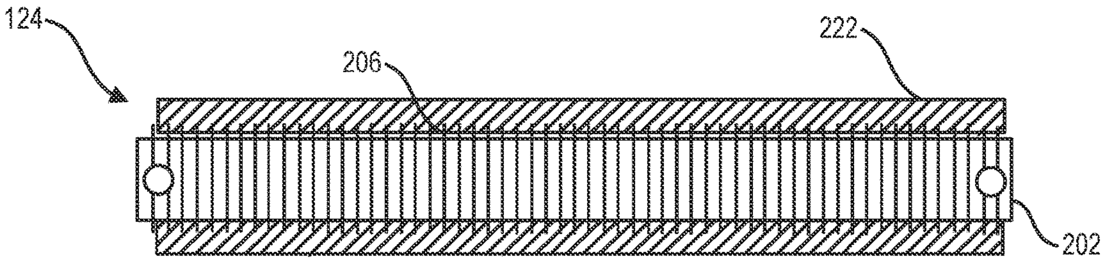

The outer thin film layer formed by the ribbon 222 may be cooled 122 and optionally reflowed to further compress the ribbon 222 between filaments of the reinforcement layer 206 into more intimate contact with the liner 202. Cooling may be performed by ambient air or a cold liquid quench, for example. After cooling, the mandrel 204 may be removed from the completed tri-layer catheter shaft construction 124 as shown in FIG. 2K. Thus, a catheter shaft may be configured with a thin film outer layer with a thickness less than 0.0015", preferably 0.0010", 0.0075", 0.0005" or even 0.0003", with corresponding tolerances of ±0.0002", 0.00013", 0.0001", and less than 0.0001", and having a continuous and uniform thin wall around the circumference of catheter shaft.

Figure 2L:
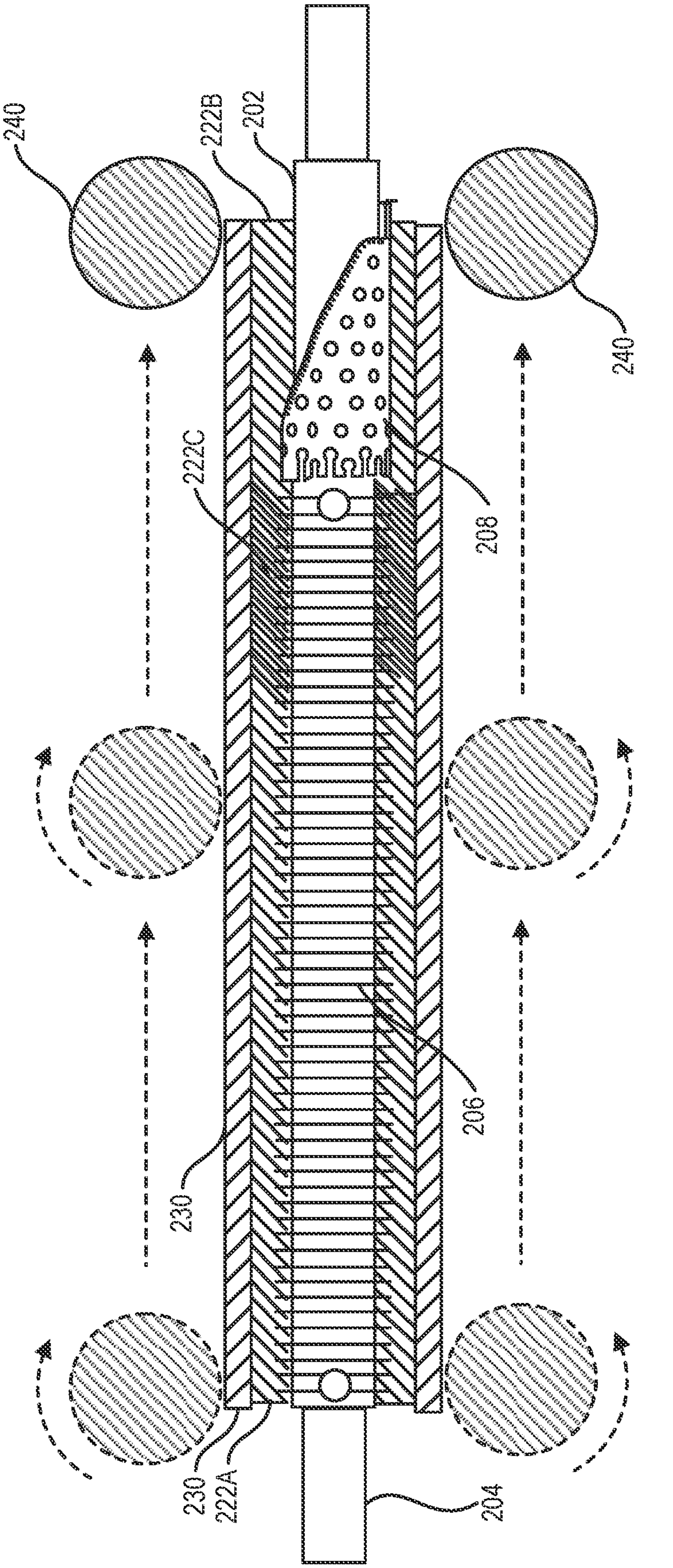

As mentioned above, reflowing may be performed to further compress the outer thin film layer and provide a connection between adjacent outer sections. For example, as shown in FIG. 2L, an additional section may be added to the tri-layer shaft assembly and reflowed using heat and compression. In this example, the tri-layer shaft construction may include a liner 202 disposed on a mandrel 204 with a reinforcement layer 206 and a first ribbon 222A outer layer assembled as described herein. Additionally, a porous substructure 208 comprising, for example, a laser-cut metallic saddle, may be connected to an end of the reinforcement layer 206 and disposed on the liner 202. A second ribbon 222B, comprising a different material or the same or similar material with different properties, may be applied as described herein to form a second thin film outer section. A compression roller 240, such as a stretched elastomeric O-ring, may be rolled over the heat-shrink tube 230 to apply additional compression while heat is applied. This may cause the first thin film outer section of ribbon 222A to reflow into the second thin film outer section of ribbon 22B creating a reflow zone of mixed ribbon material 222C. If, for example, the material of ribbon 222B is harder than the material of ribbon 222A, then the reflowed zone of mixed ribbon material 222C may have a hardness between that of ribbon 222A and 222B to provide a smooth transition is flexibility. Thus, using this reflow technique, the following results may be achieved: the outer film layer of ribbon 222A may be connected to the adjacent outer film layer of ribbon 222B via a reflow zone of mixed ribbon material 222C create a smooth transition in terms of the outer diameter and the flexibility between adjacent thin film outer sections; the outer film layer of ribbon 222A may be (further) disposed between the filaments of the reinforcement layer 206; the outer film layer of ribbon 222B may be (further) disposed in the pores of the substructure 208; the outer film layers of both ribbon 222A and 222B may be in (more) intimate contact with the liner 202.

As an alternative to connecting adjacent outer thin film layers by reflow after the ribbon 222 has been wrapped around the subassembly 112, different ribbons (in terms of composition or physical properties, such as hardness, for example) may be connected beforehand. Two or more ribbons may be connected by overlap welding or butt welding, for example. Such connection may be made when the thin film is in the form of a sheet (i.e., before the ribbon is cut), or when the thin film is in the form of a ribbon. For purposes of illustration, not limitation, the connection is described with reference to a thin film sheet.

Figure 3A:
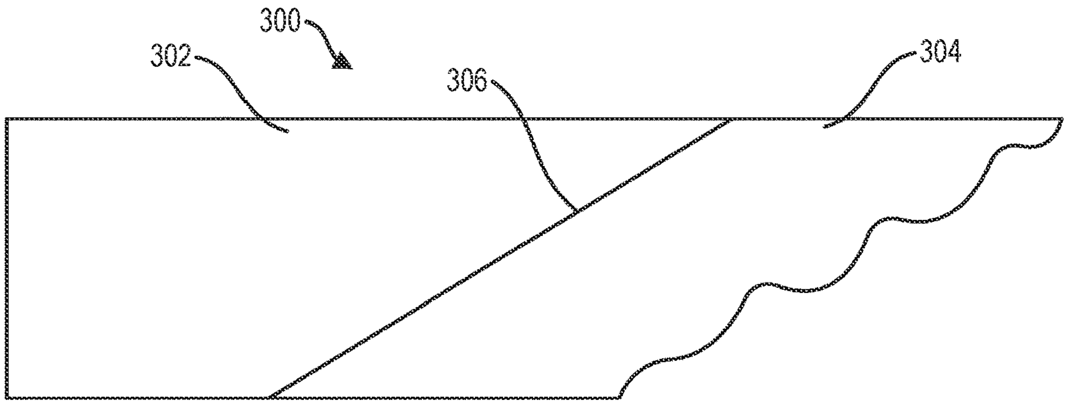
FIGS. 3A-3I are schematic illustrations of parts and manufacturing methods according to another embodiment of the present disclosure for joining thin film sheets end-to-end for use on a catheter or portion thereof.

Turning to FIG. 3A, thin film sheet 300 includes a first thin film sheet section 302 positioned to abut a second thin film sheet section 304 along an edge 306. An abutting joint may be preferred over an overlapping joint to minimize profile. The first section 302 may comprise a first material and the second section 304 may comprise a second material, where the first material is different from the second material in terms of composition, dimensions or properties. For example, the first section 302 may be formed of a PEBAX and the second section 304 may be formed of VEASTAMID. Alternatively, the first section 302 and the second section 304 may be formed of the same or similar polymers but with different properties such as hardness, radiodensity or color, for example. Or the first section 302 may have a different wall thickness than the second section 304. These differences may be taken alone or in combination, depending on the desired properties of the catheter.

The edge 306 may be configured at a right angle or at an acute angle, such as 45 degrees as shown, for example. An angled edge 306 provides more contact surface area between the first 302 and second 304 thin film sheet sections to enhance bond strength, for example. In addition, when cut into a ribbon and configured into a layer of a catheter shaft, an angled edge 306 may provide a gradual transition between the first 302 and second 304 thin film sections, thus providing a gradual transition in properties such as flexibility, for example.

Where the edges of adjacent thin film sections come together, a circumferential joint or seam may be formed, although perhaps not visible, where the material of adjacent sections flows together. When incorporated into a catheter or portion thereof and viewed from the side, the circumferential joint or seam may appear as a circle around the perimeter of the catheter if the edge is configured at a right angle, or an oval around the perimeter of the catheter if the edge is configured at an acute angle. The number and spacing of such joints may be a function of the number and spacing of sections used. When different colored sections are used, the joint may be used to inform the user how far the catheter extends into another catheter, for example. This may be helpful when advancing or retracting the catheter inside another catheter, for example, and may indicate anatomical position of the catheter.

Figure 3B:
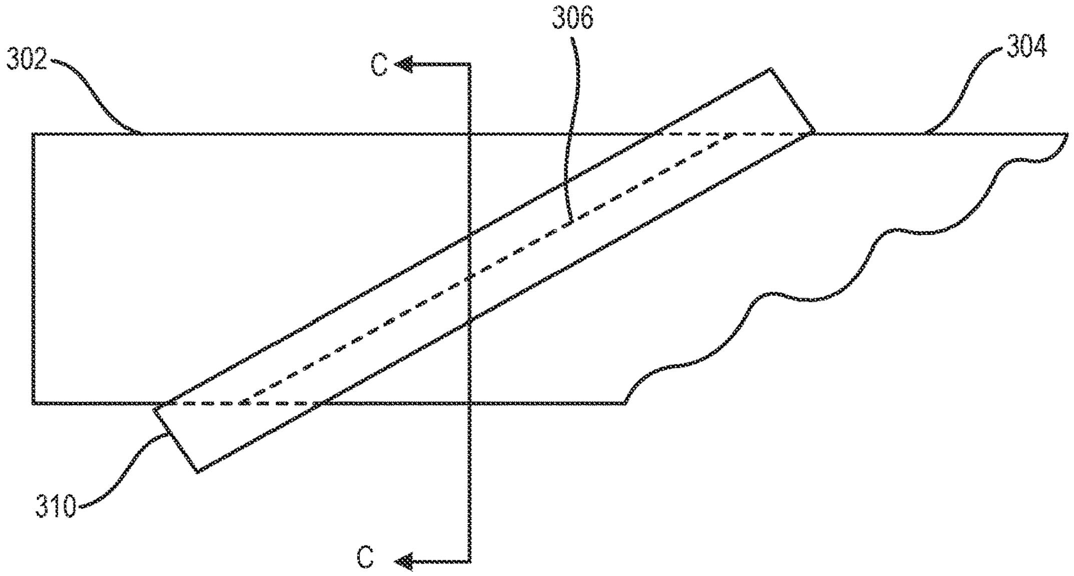
Figure 3C:
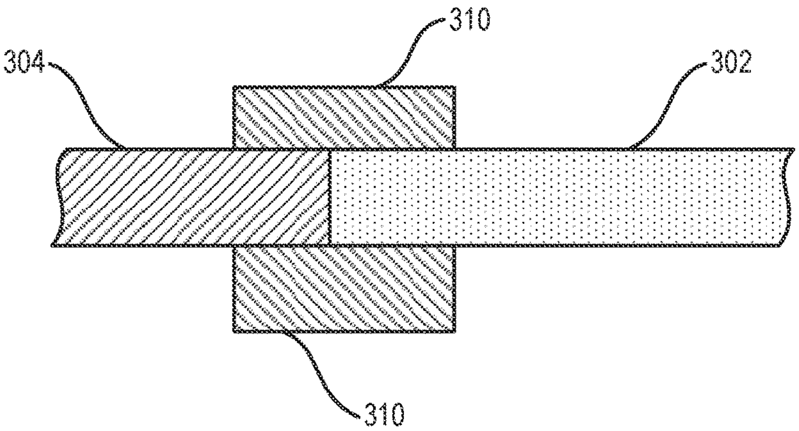
Figure 3D:
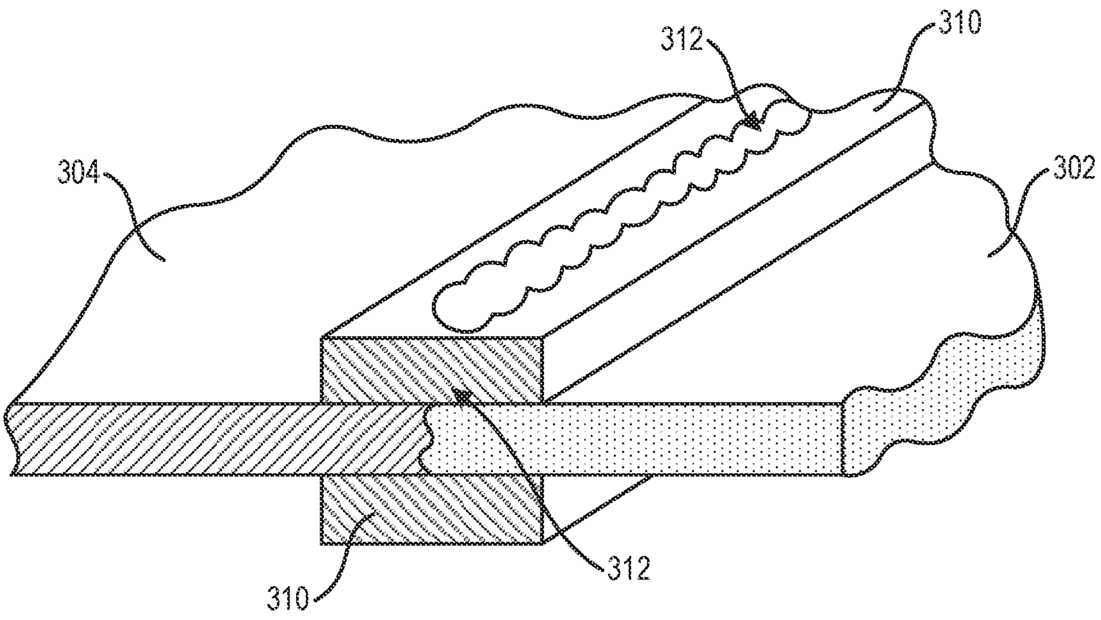

As shown in FIG. 3B, as well as FIG. 3C which is a cross-sectional view taken along line C-C in FIG. 3B, the first 302 and second 304 thin film sheet sections may be held in place by blocks 310 on either side of the sheets 302, 403 such that the edges of the thin film sheet sections 302, 304 remain in intimate contact. Pressure and heat may then be applied to along the edge 306 to bond the first 302 and second 304 thin film sheet sections together to form a seam at edge 306. Pressure may be applied by compression via blocks 310, for example. Sufficient heat may be applied to cause both the edges of the first 302 and second 304 sheet sections to be at a temperature above their respective glass transition temperatures. Thermal energy may be applied by convectively (e.g., hot air gun), conductively (e.g., heated block) or radiantly (e.g., laser or heat lamp), for example. As shown in FIG. 3D, the blocks 310 may include windows 312 through which heat (e.g., laser) may be transmitted to the edge 306 while acting as a heat sink for adjacent areas.

Figure 3E:
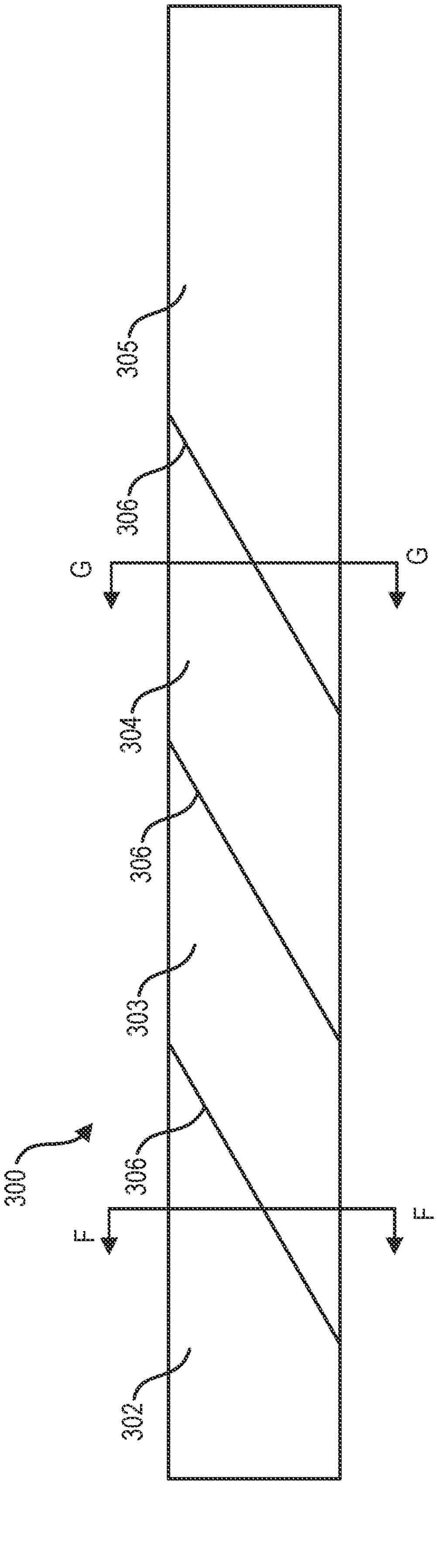
Figure 3G:
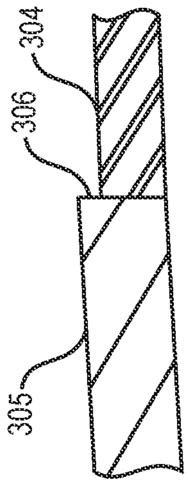
Figure 3F:
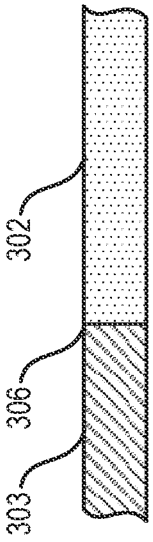

FIGS. 3A-3D illustrate a single seam formed along edge 306 between two sheet sections 302 and 304. The same principles may be applied to any desired number of sheet sections. For example, in FIGS. 3E, 3F and 3G, an example of a thin film sheet comprising four sections is shown schematically. FIGS. 3F and 3G are cross sectional views taken along lines F-F and G-G, respectfully, in FIG. 3E. Each of thin film sheet sections 32, 303, 304 and 305 may comprise different materials, properties or dimensions, which allows catheters to be further customized along their length for purposes of flexibility, radiodensity, color, etc. and ultimately for better performance. By way of example, not limitation, sheet section 302 may incorporate radiopaque loading for enhanced visibility under fluoroscopy, sheet section 303 may comprise the same or similar material as sheet section 302 but be free of radiopaque loading, sheet section 304 may comprise the same or similar material as sheet section 303 but with a higher hardness for enhanced pushability, and sheet section 305 may comprise the same or similar material as sheet section 304 but with a greater wall thickness for enhanced rigidity.

Figure 3H:
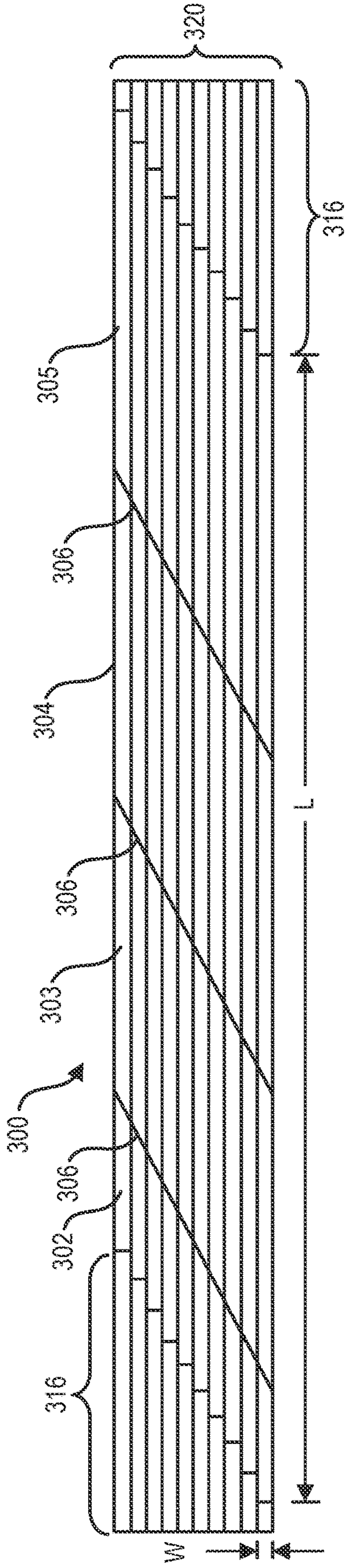
Figure 3I:
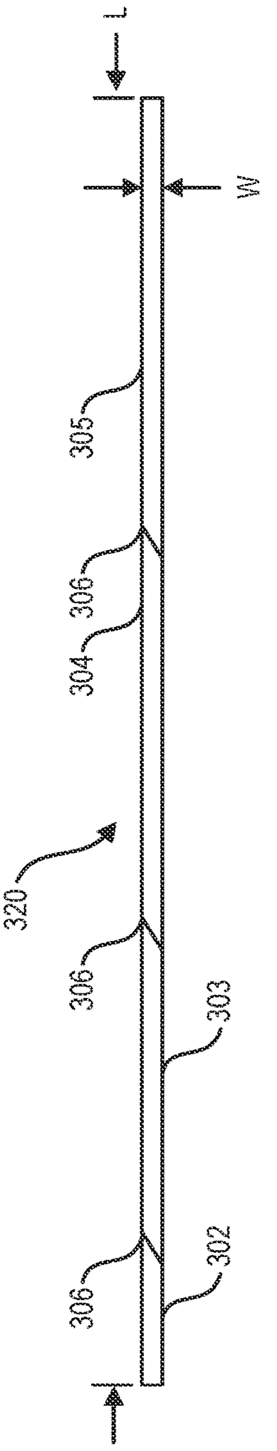

As mentioned herein, the connections between sections may be made when the thin film is in the form of a sheet (i.e., before the ribbons are cut). FIG. 3H schematically illustrates a top view of a sheet 300 with four sheet sections 302, 303, 304, and 305 that may be cut into a plurality of ribbons 320, each with the same or similar length (L), width (W) and proportions of sections 302, 303, 304, and 305 as shown in FIG. 3I. To achieve this, the four sheet sections 302, 303, 304, and 305 may be connected as described above. Longitudinal cuts may be made through the sheet as described previously to define the width W of each ribbon 320. Because the edges 306 of adjacent sheet sections are configured at an angle, staggered end cuts may be made for each ribbon 320, resulting in scrap sections 316, ribbons 320 of equal length L, and sections 302, 303, 304, and 305 of equal length. The ribbons 320 may then be constructed into a catheter or layer thereof as described previously.

Figure 4A:
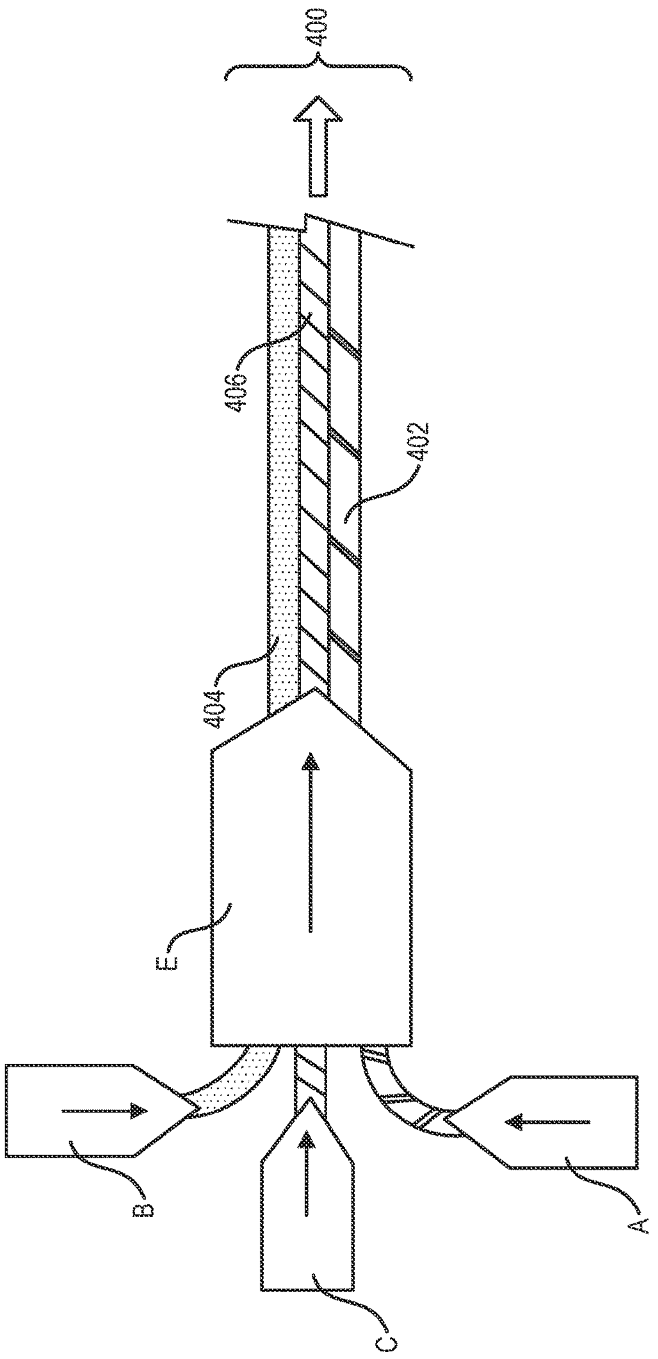
FIGS. 4A-4D are schematic illustrations of parts and manufacturing methods according to yet another embodiment of the present disclosure for making multi-layered thin film sheets or modified thin film sheets for use on a catheter or portion thereof.
Figure 4B:
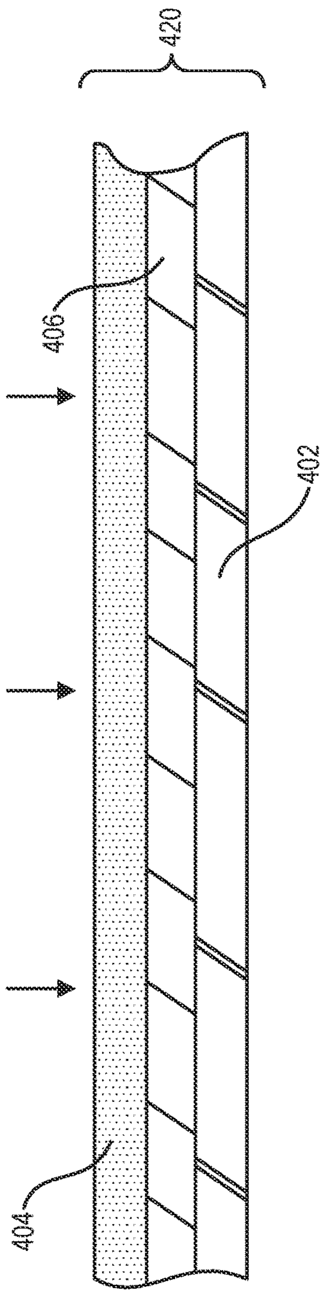
Figure 4C:
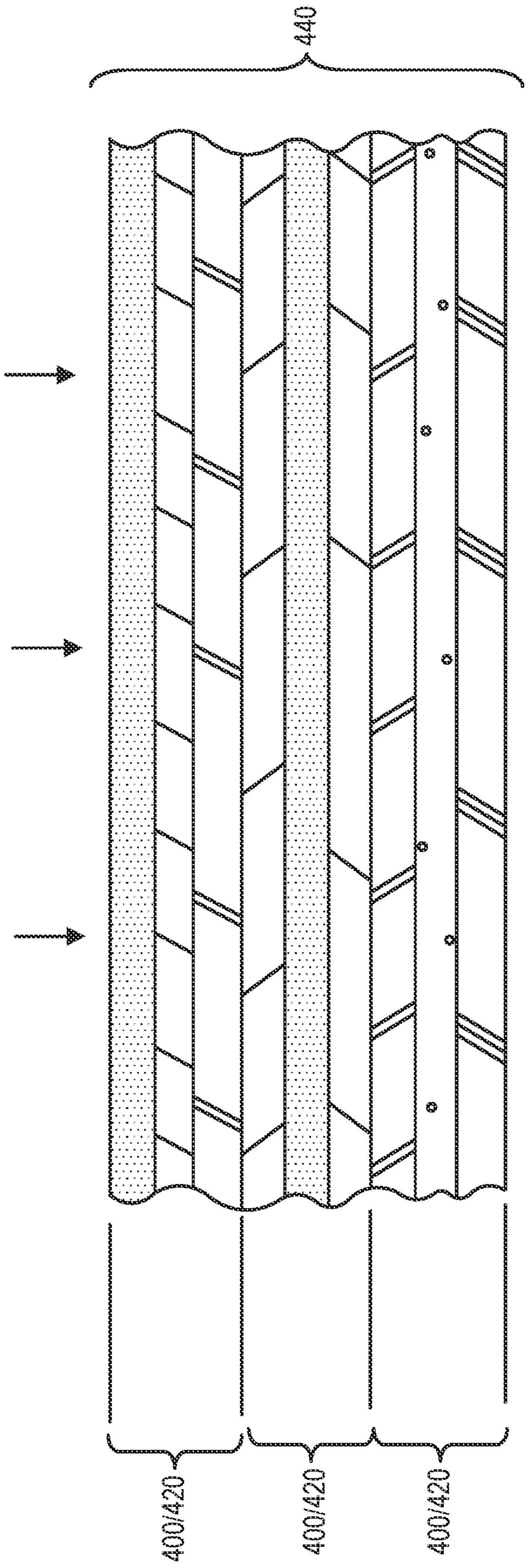

In addition to providing different sections of thin film along a length of sheet or ribbon as described above, different sections of thin film may be provided across the width or thickness of a thin film sheet or ribbon. For example, different sections of thin film may be provided across the thickness of a thin film sheet or ribbon using multiple layers, which may comprise a coextruded a thin film sheet 400 as schematically shown in FIG. 4A, a laminated thin film sheet 420 as schematically shown in FIG. 4B, or a composite thin film sheet 440 as schematically shown in FIG. 4C. The composite thin film sheet 440 may comprise a lamination of coextruded thin film sheets 400 or laminated thin film sheets 420. Each thin film layer of the coextruded 400, laminated 420 or composite 440 multilayer sheet may be selected to have a specific property such as strength, hardness, flexibility, radiopacity, lubricity and/or color, for example. Further, the multilayered sheets 400, 420 or 440 may comprise sheet sections connected end-to-end as described previously. The multilayered sheets 400, 420 or 440 may be formed into ribbons and incorporated into a catheter or layer thereof as described previously.

With reference to FIG. 4A, and by way of example, not limitation, a lubricious polymer (e.g., PTFE or HDPE) may be loaded into hopper A, a radiopaque loaded PEBA or VESTAMID may be loaded into hopper B, and a tie material may be loaded into hopper C. The three materials may pass through extruder E to form a co-extruded tri-layer sheet 400 with a lubricious inner layer 402, a radiopaque outer layer 404 and a tie layer 406. Tie layer 406, which may comprise a blend of the inner and outer materials or a material with sticky characteristics, may aid in adhering the interfaces between the inner 402 and outer 404 layers and mitigate delamination when is use. The rheology of the grades of materials for each layer may be closely matched to ease co-extrusion.

With reference to FIG. 4B, the same or similar layers 402, 404 and 406 may form a laminated sheet 420. The layers of the laminated sheet may be bonded by application of heat and pressure. Pressure may be applied by compression blocks (not shown) disposed on both sides of the sheet 420 surface, for example. Heat may be applied on the entire surface or at discrete locations to define spot welds using a suitable heat source and masking plate, for example.

With reference to FIG. 4C, the multi-layer sheets 400 or 420 may form a composite sheet 440. In this example, tri-layer sheets formed by co-extrusion 400 or lamination 420 may be stacked and laminated using the same or similar application of heat and pressure as described above. In addition, the composite sheet 440 may be laminated under vacuum conditions to remove any gas that may be trapped between layers.

Figure 4D:
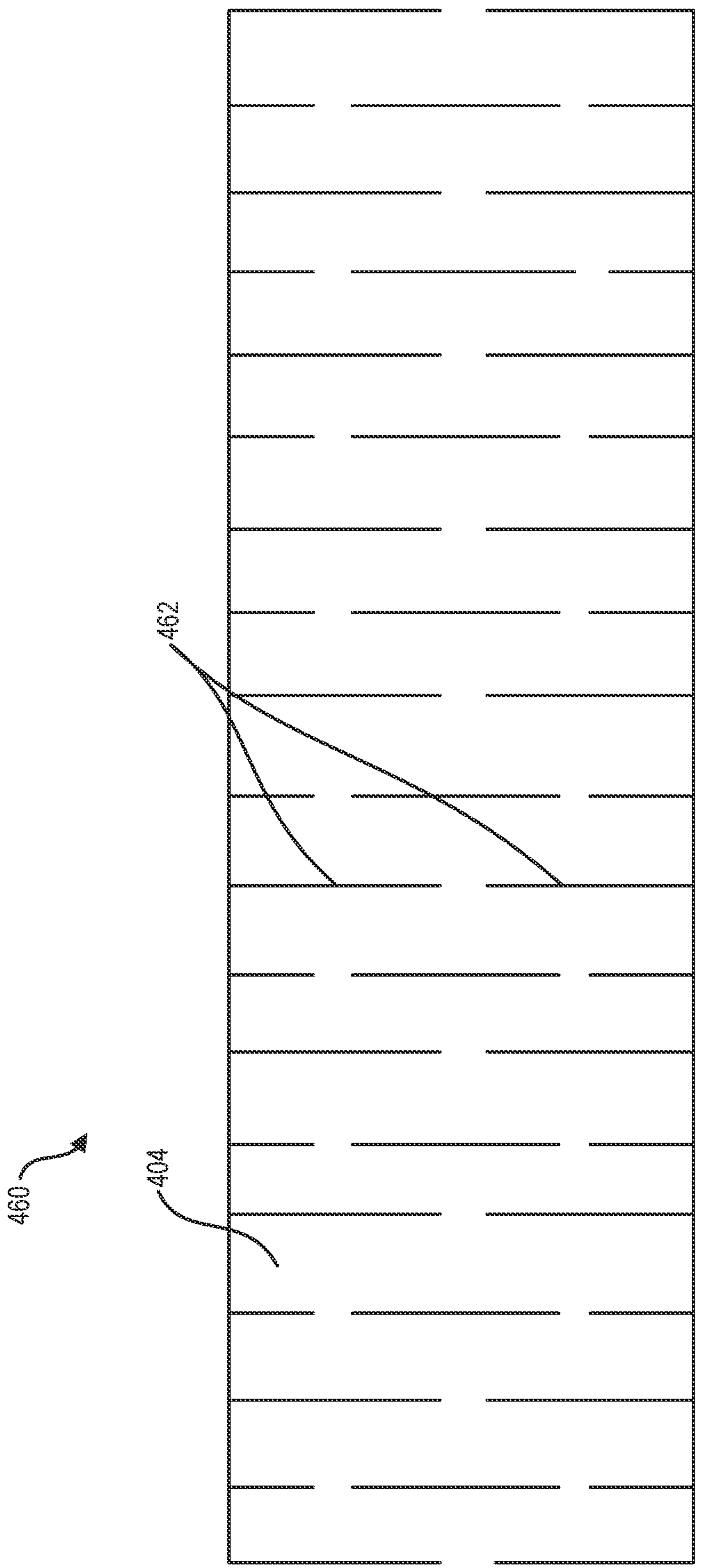

Each thin film sheet or ribbon may be chemically or physically modified to alter its properties. For example, a thin film sheet or ribbon may incorporate a surface modification (e.g., plasma treatment, roughened) to enhance its adherence to other layers. Alternatively, a thin film sheet or ribbon may have a portion of material removed, wherein the portion removed extends partially or completely through the thickness of the film. For example, a modified thin film sheet 460 may incorporate divots, holes, grooves or slots 462 as schematically shown in FIG. 4D. Such features may extend partially or completely through the thickness of the film 404. The features may be formed in a manner similar to how the ribbon is cut from the thin film sheet as described previously, using a laser and masking template. In the illustrated example, the slots 402 may comprise cuts that extend through the thickness of the thin film 404 in a discontinuous circumferential pattern to impart additional flexibility along its length while retaining structural integrity, for example.

Such features may be made in a single thin film layer or a multilayer thin film. In the latter instance, the features may be made in an inner or outer layer, where the middle layer has different properties that make it less susceptible to the material removal process. For example, the material of the middle layer may have a higher melt temperature than the material of the inner or outer layer such that thermal ablation (e.g., laser cutting) forms the feature in the inner and/or outer layer but not the middle layer with an appropriately set ablation temperature. This general approach may be applied to any single layer, any combination of layers or all the layers. The layer or layers having the modification (e.g., cut pattern) may have a higher glass transition temperature than the other layers such that the modified layers retain the modification during assembly onto a catheter shaft by heat and compression. Further, any layer with an exposed surface (inside or outside) may incorporate a lubricious coating (e.g., silicone, hydrophilic polymer).

The constructions, features, and manufacturing techniques described herein may be incorporated, in whole or in part, taken alone or in combination, into a variety of catheters such as coronary, peripheral and neuro guide catheters, guide catheter extensions, diagnostic catheters, aspiration catheters, microcatheters, balloon catheters, stent delivery catheters and the like, whether femoral access, radial access or other access, some examples of which are described herein. The table below illustrates how thin film tubes may be implemented in a variety of intravascular catheters, and the percent (%) improvement in wall thickness between conventional (prior art) devices and new (present disclosure) devices.

| Device | | Distal OD | ID | Wall | % Thinner |
|---|---|---|---|---|---|
| Diagnostic | Conventional | 5F | 0.045-.047" | 0.009" | |
| Catheter | New | 5F | 0.060" | 0.003" | 67% |
| Guide | Conventional | 6F | 0.070-0.071" | 0.0045" | |
| Catheter | New | 6F | 0.075" | 0.003" | 33% |
| Guide | Conventional | 6F | 0.056-0.057" | 0.005" | |
| Catheter Ext. | New | 6F | 0.061" | 0.003" | 40% |
| Micro- | Conventional | 1.8F | 0.0155" | 0.004" | |
| Catheter | New | 1.4F | 0.0155" | 0.0022" | 45% |
| Balloon | Conventional | 2.5F | | 0.005" | |
| Catheter | | (0.033") | | | |
| | New | 1.9F | | 0.003" | 40% |
| | | (0.025") | | | |
| Aspiration | Conventional | 6F | 0.068" | 0.006" | |
| Catheter | New | 6F | 0.074" | 0.003" | 50% |

Figure 5A:
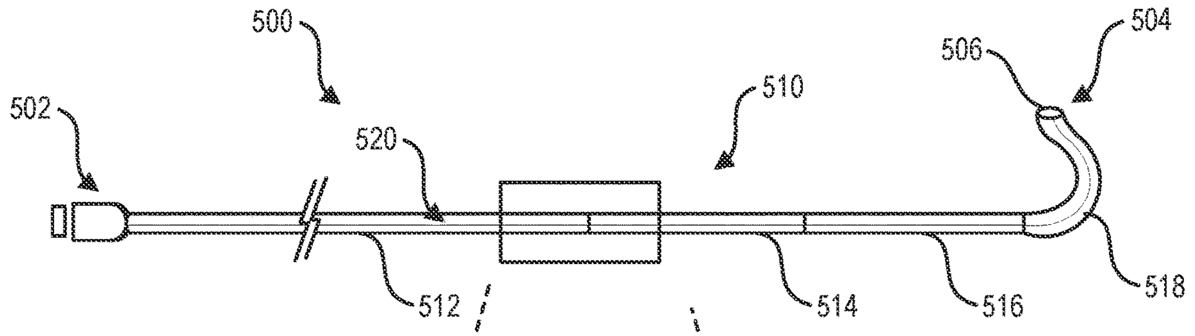
FIGS. 5A-5E are schematic illustrations of guide or diagnostic catheters incorporating a thin film according to an embodiment of the present disclosure.

For example, as shown in FIG. 5A, a guide or diagnostic catheter 500 may incorporate the constructions described herein. Catheter 500 may include a proximal portion 502 with a hub and a distal portion 504 with an optional pre-set curve configured for the particular anatomy being accessed. Catheter 500 may include a tubular shaft 510 with a lumen 508 extending therethrough from the proximal portion 502 to the distal portion 504 ending in a distal facing opening 506.

Figure 5B:
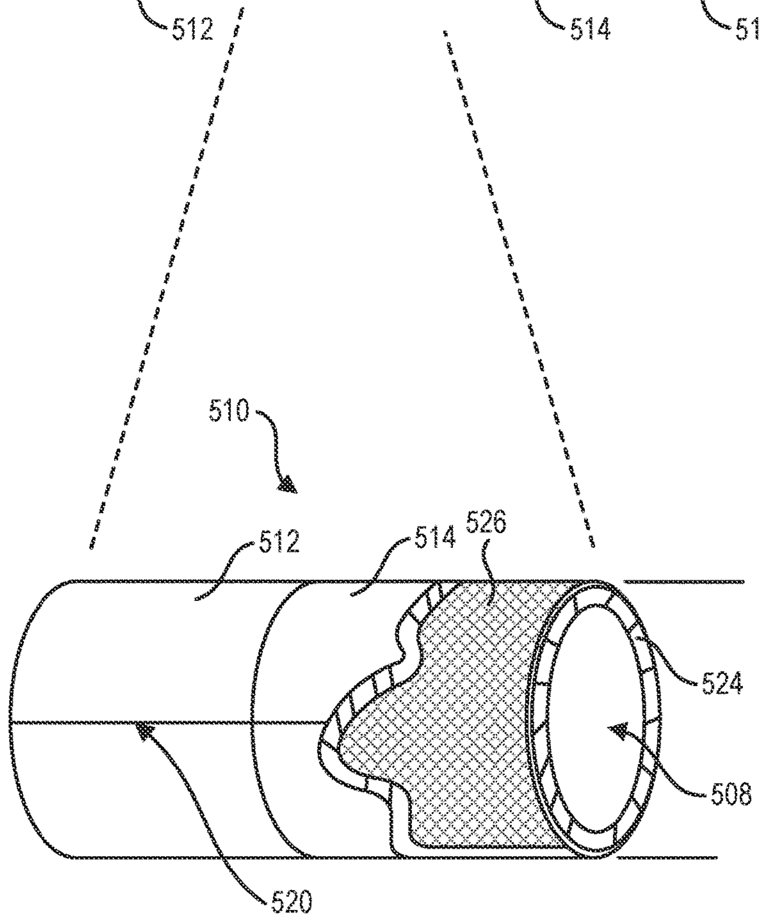

As best seen in FIG. 5B, which is a partially sectioned detail view of the boxed portion shown in FIG. 5A, the catheter shaft 510 may comprise an inner liner 524 such as thin-walled PTFE over which a reinforcement layer 526 such as braid may be disposed. The outer layer may comprise a series of thin film sections 512, 514, 516 and 518 of the same or similar material with decreasing hardness from proximal to distal. The outer layer may be constructed as described herein to form a longitudinal joint or seam 520, as well as circumferential joints or seams between each of the thin film sections 512, 514, 516 and 518.

Figure 5C:
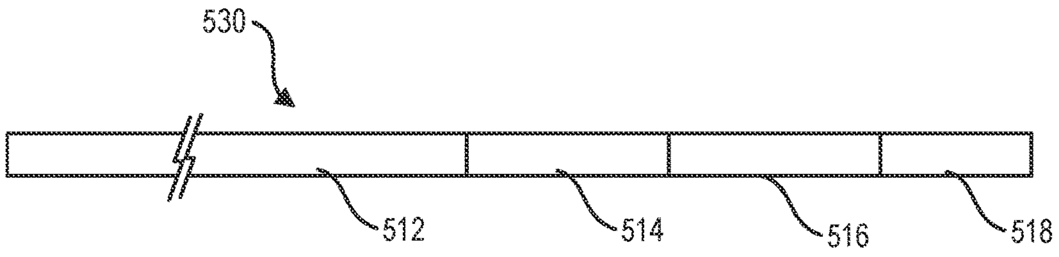
Figure 5D:
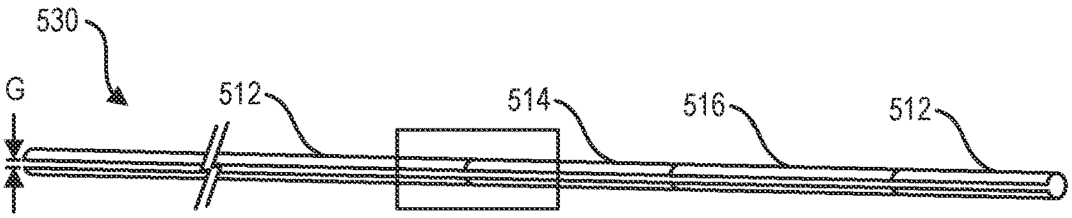
Figure 5E:
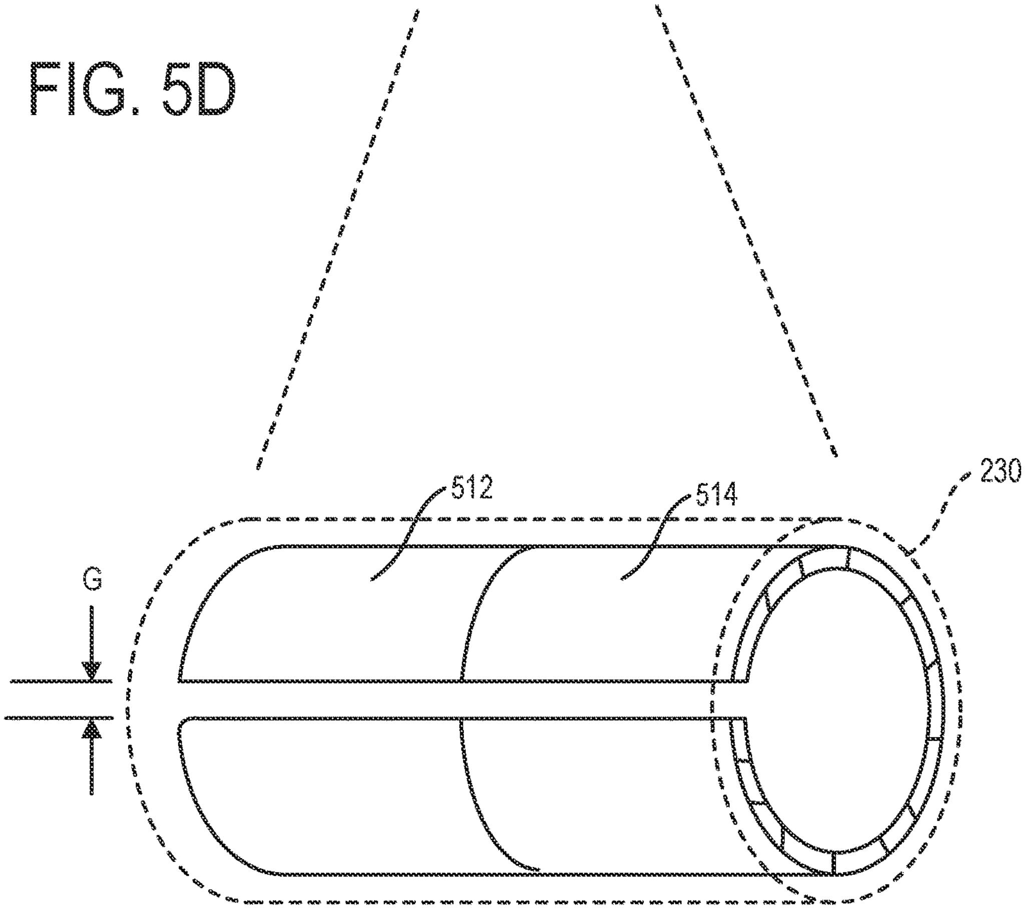

For example, with reference to FIG. 5C, a thin film ribbon 530 may be formed from a sheet comprising a series of thin film sections 512, 514, 516 and 518. The ribbon 530 may be rolled to define a gap G as shown in FIG. 5D, as well as FIG. 5E which is a partially sectioned detail view of the boxed portion shown in FIG. 5D. The ribbon 530 may be placed in a carrier 230 comprising, for example, a heat shrink tube, and loaded onto a subassembly comprising liner 524 and reinforcement layer 526. Applying heat and compression conforms the ribbon 530 around the subassembly, closes the gap G, and forms a longitudinal joint 520 along the longitudinal edges of the ribbon 530.

By using a thin film outer layer with a thickness less than 0.0015", preferably 0.0010" 0.0075", 0.0005" or 0.0003", for example, the density (e.g., picks per inch or PPI) of the reinforcement layer (e.g., braid) 526 may be increased and the inside diameter of the through lumen 508 may be increased to improve performance without compromising the profile of the catheter 500. For example, a conventional 6F catheter may have an outside diameter of 2 mm or 0.0786", an extruded inner liner wall thickness of 0.0015", a braid thickness of 0.005" (0.00075" thick wire braided at 60 PPI) and an extruded outer covering having a wall thickness of 0.0038", resulting in an inside diameter of 0.071". By contrast, by using a thin film for the outer covering having a wall thickness of 0.00075" to 0.001", for example, the braid density may be increased to 120-180 PPI using the same wire and inner liner, resulting in a larger inside diameter of 0.074". The thin film outer covering generally allows the precise application of ultra-thin conformal coatings such that additional reinforcement support structure can be added and the inside diameter may be enlarged to improve performance without increasing the size (outside diameter) of the catheter 500.

Figure 6A:
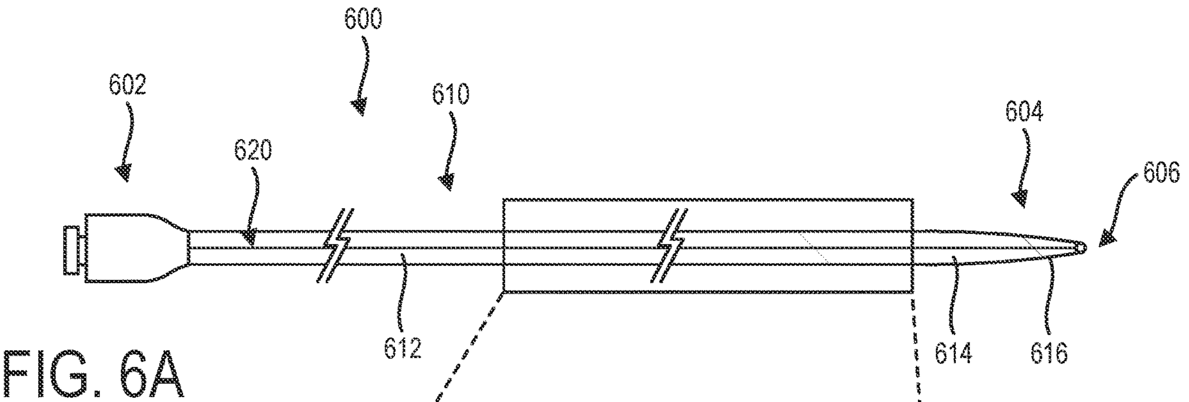
FIGS. 6A-6H are schematic illustrations of microcatheters incorporating a thin film according to an embodiment of the present disclosure.

With reference to FIG. 6A, a microcatheter 600 may incorporate the constructions described herein. Microcatheter 600 may include a proximal portion 602 with a hub and a distal portion 604 that may optionally be tapered as shown, for example. Microcatheter 600 may include a tubular shaft 610 with a lumen 608 extending therethrough from the proximal portion 602 to the distal portion 604 ending in a distal facing opening 606.

Figure 6B:
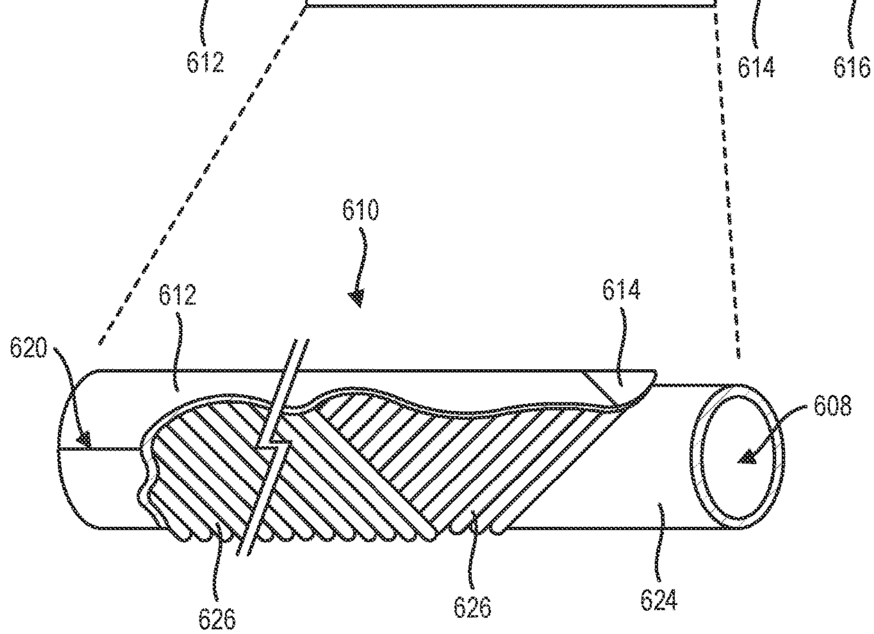
Figure 6C:
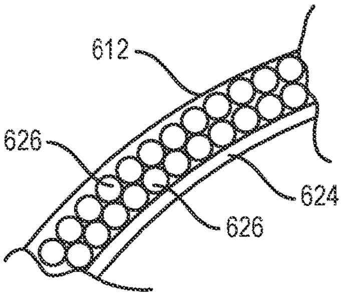

As best seen in FIG. 6B, which is a partially sectioned detail view of the boxed portion shown in FIG. 6A, the catheter shaft 610 may comprise an inner liner 624 such as thin-walled PTFE over which a reinforcement layer 626 such as a coil may be disposed. The outer layer may comprise a series of thin film sections 612, 614 and 616 of the same or similar material with decreasing hardness from proximal to distal. As seen in FIG. 6C, which illustrates a partial section of the catheter shaft 610 wall, the thin film outer layer allows the use of additional reinforcement material 626, such as two layers of counter-wound coil, without increasing the profile of the microcatheter 600. The outer layer may be constructed as described herein to form a longitudinal joint or seam 620, as well as circumferential joints or seams between each of the thin film sections 612, 614 and 616.

Figure 6D:
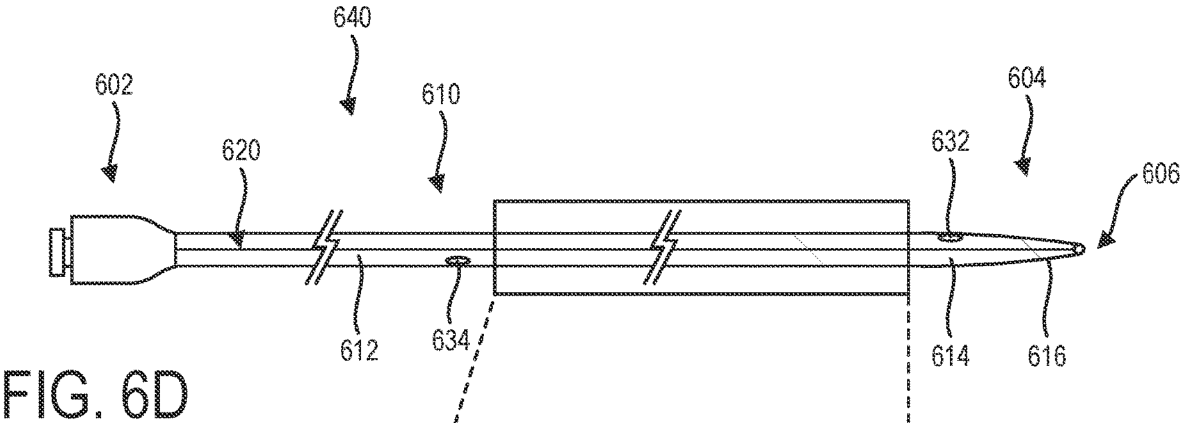
Figure 6E:
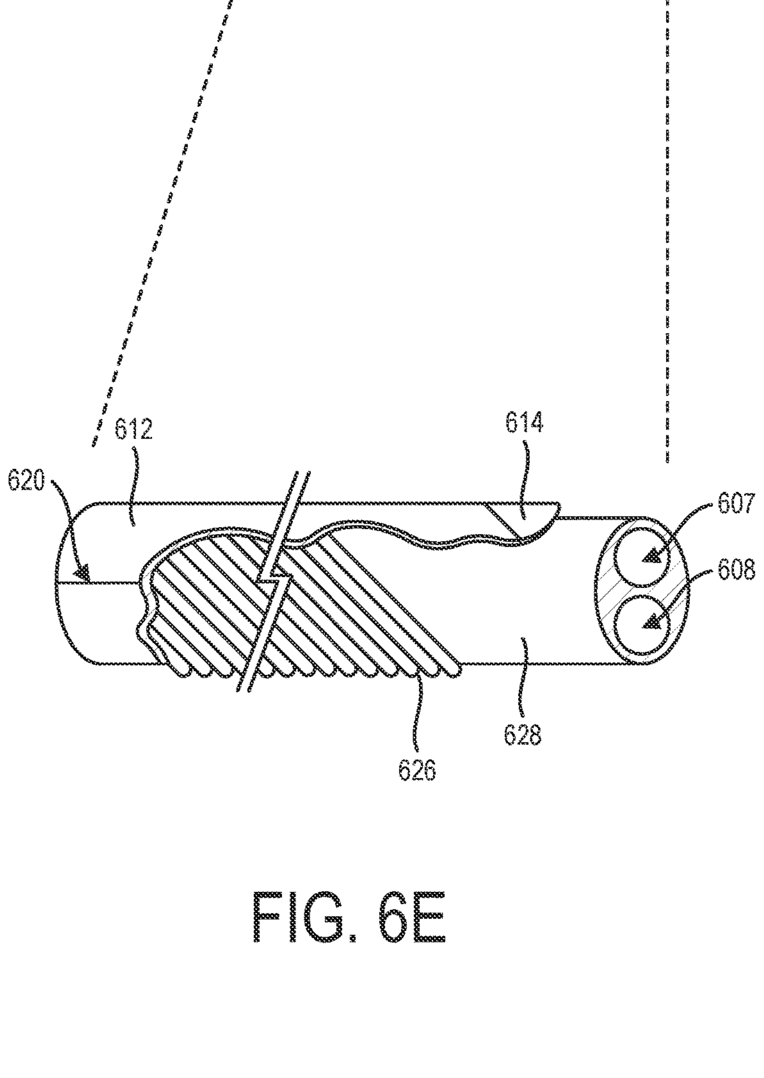

Whereas the microcatheter 600 uses a single lumen 608 that may accommodate a guidewire or be used for delivering fluids and devices, microcatheter 640, shown schematically in FIG. 6D, uses two lumens 607 and 608. In this example, a dual lumen extrusion 628 may replace the inner liner 624 described with reference to FIG. 6A. The catheter shaft 610 may include a proximal port 634 that provides access to lumen 608 wherein a guidewire may extend proximally out of port 634, distally through lumen 608, and distally out of the distal facing opening 606. This dual lumen and side port configuration may be referred to as monorail, rapid exchange, etc., and may be used for exchanging the catheter 640 over a conventional length guidewire. The catheter shaft 610 may also incorporate a distal port 632 in fluid communication with lumen 607 and the hub on proximal portion 602. This configuration allows liquids and devices to be delivered without removal of a guidewire disposed in lumen 608.

Figure 6F:
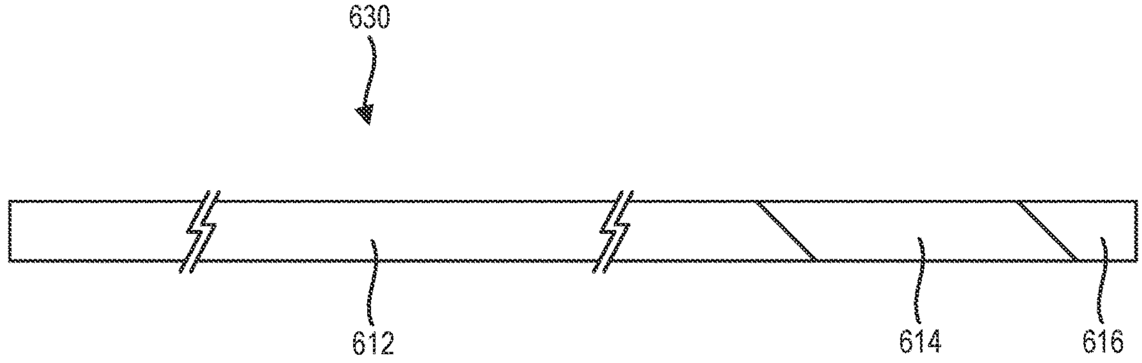
Figure 6G:
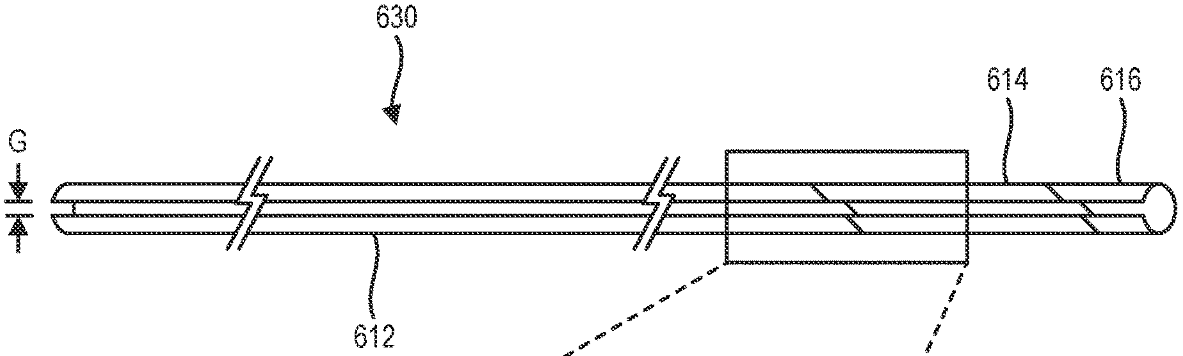
Figure 6H:
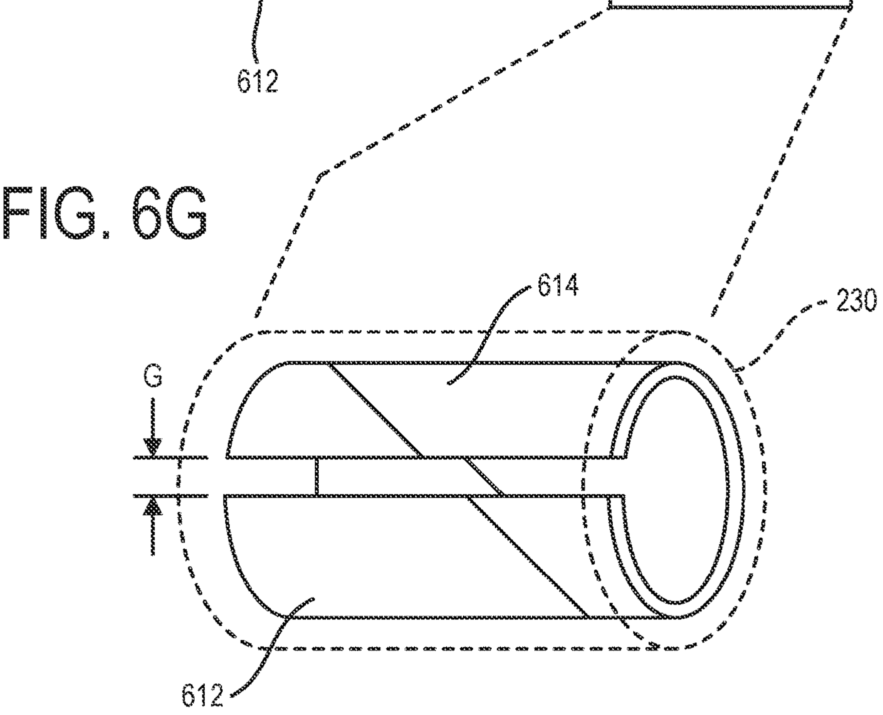

For both microcatheter 600 and 640, and with reference to FIG. 6F, a thin film ribbon 630 may be formed from a sheet comprising a series of thin film sections 612, 614, and 616. The ribbon 630 may be rolled to define a gap G as shown in FIG. 6G, as well as FIG. 6H which is a partially sectioned detail view of the boxed portion shown in FIG. 6G. The ribbon 630 may be placed in a carrier 230 comprising, for example, a heat shrink tube, and loaded onto a subassembly comprising liner 624 and reinforcement layer 626, or comprising dual lumen extrusion 628 and reinforcement layer 626. Applying heat and compression conforms the ribbon 630 around the subassembly, closes the gap G, and forms a longitudinal joint 620 along the longitudinal edges of the ribbon 630.

A distal portion of the reinforcement layer 626 may comprise a more radiopaque material than a proximal portion of the reinforcement layer to facilitate fluoroscopic navigation. For example, a radiopaque coil comprising a rectangular ribbon (e.g., 0.005"×0.0015") with a tantalum core (approximately 40% by cross sectional area) and a jacket of spring temper MP35N or stainless-steel may be used. In this example, the jacket material may have an X-ray attenuation coefficient less than 50 l/cm and the core material may have an X-ray attenuation coefficient greater than the 50 l/cm. The tantalum core provides radiopacity and the MP35N or stainless-steel jacket provides structural integrity and is weldable. The coil may have a variable pitch wind such that a low pitch (e.g., no gap) portion provides more radiodensity and a higher pitch portion provides more flexibility.

Figure 7A:
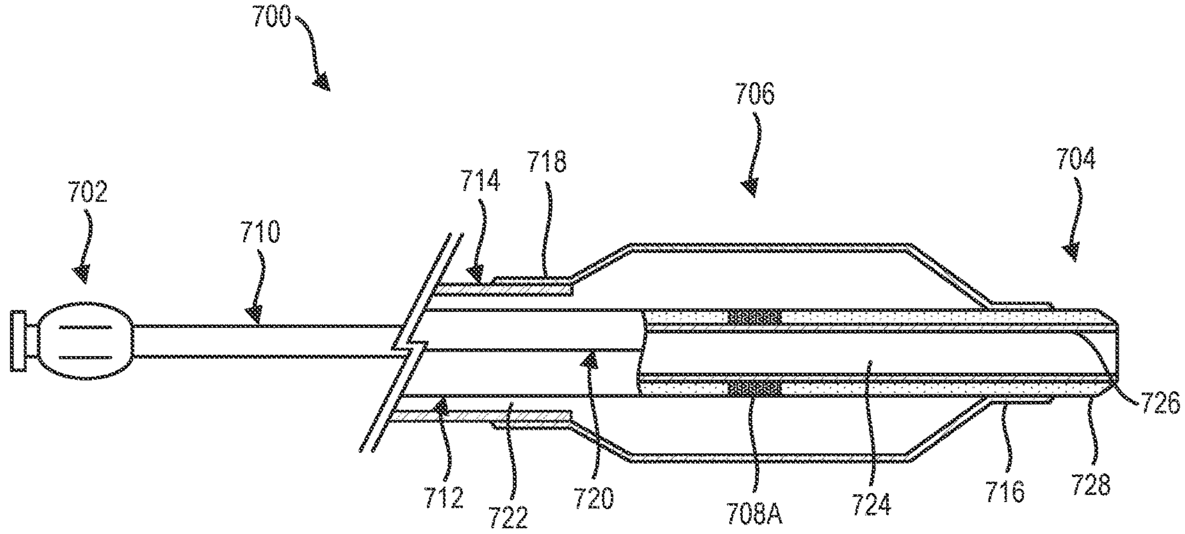
FIGS. 7A-7B are schematic illustrations of balloon catheters incorporating a thin film according to an embodiment of the present disclosure.
Figure 7B:
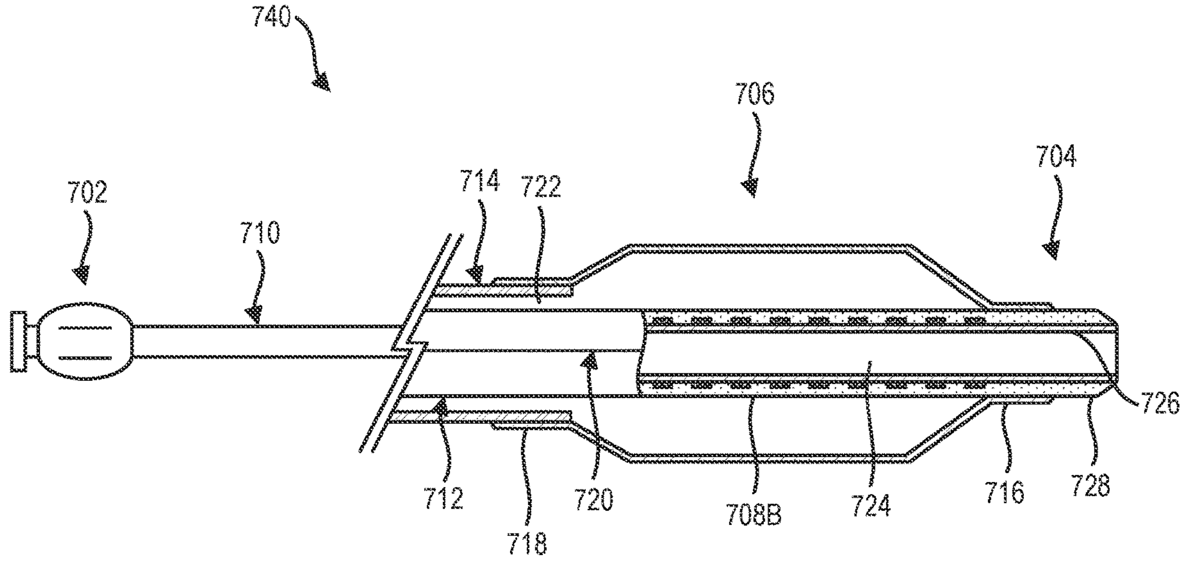

With reference to FIG. 7A, a balloon angioplasty catheter 700 may incorporate the constructions described herein. The balloon angioplasty catheter 700 may be used for plain old balloon angioplasty (POBA) or for stent delivery, for example. The balloon catheter 700 may comprise a fixed-wire, over-the-wire, or rapid exchange construction as shown. The balloon catheter 600 may include a proximal portion 702 with a hub or manifold and a distal portion 704 that may optionally be tapered as shown, for example. The balloon catheter 700 may include a tubular shaft 710 comprising an inner 712 and an outer 714. A balloon 706 may be connected to the shaft 710 with a proximal waist 718 connected to the outer and a distal waist 716 connected to the inner 712. The inner 712 may define a guidewire lumen 724 and an inflation lumen 722 may be defined in the annular space between the inner 712 and outer 714 for inflation and deflation of the balloon 706. The inner 712 may include a lubricious liner 726 (e.g., PTFE or HDPE) and a jacket 728 (e.g., PEBAX or VESTAMID). A radiopaque marker band 708A may be disposed between the liner 726 and a jacket 728. Alternatively, a support structure 708B (e.g., a coil of flat metal ribbon which may be radiopaque) may be disposed between the liner 726 and a jacket 728 as shown on balloon catheter 740 illustrated in FIG. 7B.

Both the liner (inner) layer 726 and the jacket (outer) layer 728 of the inner tube 712 may comprise a thin film ribbon that is wrapped, heated and compressed to form joint or seam 720 as described herein. By using thin film ribbon, the inner 712 may have an ultra-thin wall, enabling a smaller distal balloon waist 716 for the same size guidewire lumen 724. This reduces the crossing profile of the balloon catheter 700/740 enabling it to cross tight vascular restrictions such as those encountered in chronic total occlusions (CTOs) and generally in very small caliber anatomy.

Figures 8A, 8B:
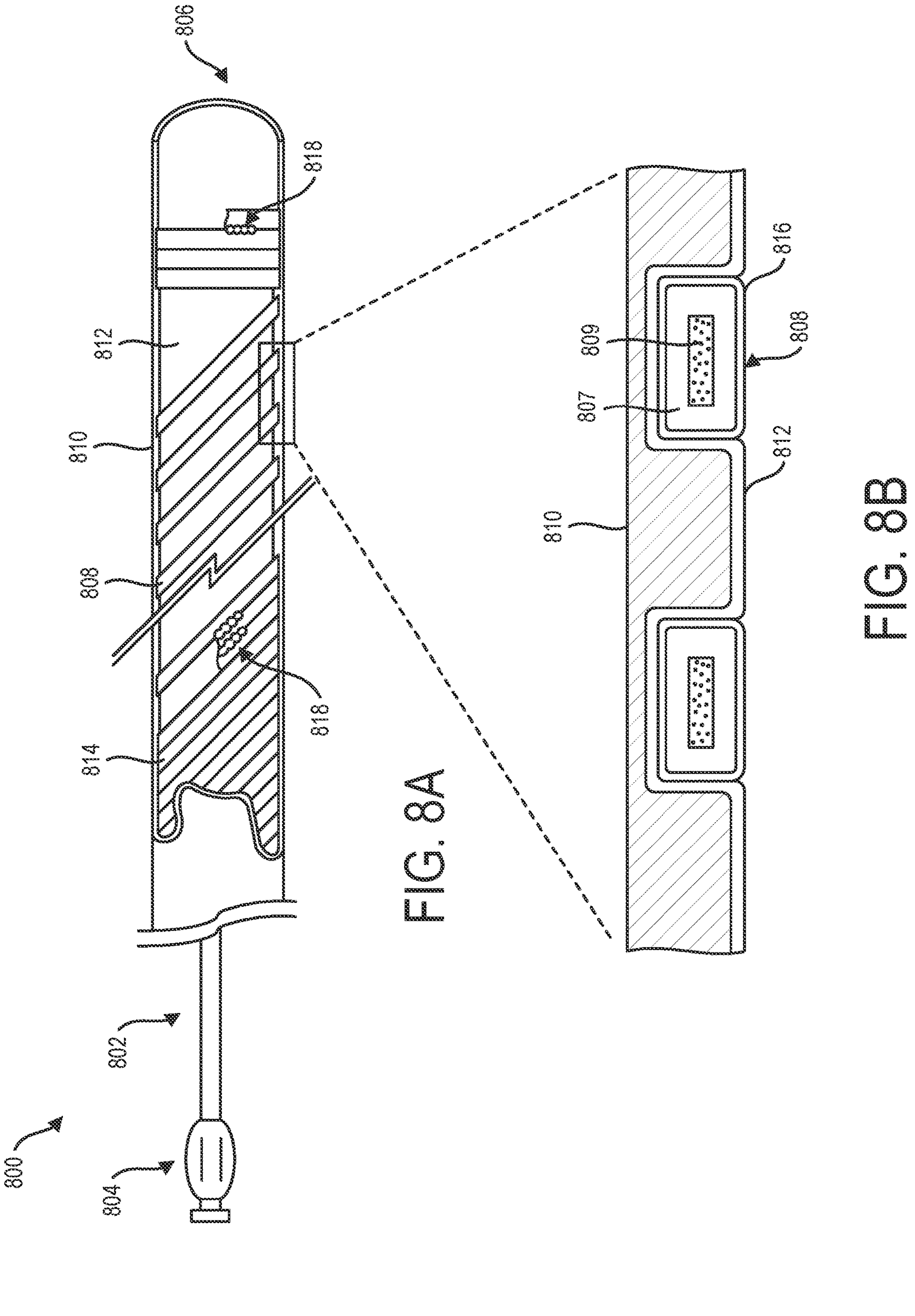
FIGS. 8A-8B are schematic illustrations of an aspiration catheter incorporating a thin film according to an embodiment of the present disclosure.

With reference to FIG. 8A, an aspiration catheter 800 may incorporate the constructions described herein. Aspiration catheter 800 may include an elongate tubular shaft 802 defining an aspiration lumen therein for removal of vascular thrombus, fibrin clot or the like. The aspiration lumen may extend from a hub 804 connected to the proximal end of the shaft 802 (for connection to a pump) to a distal opening 806 at the distal end of the shaft 802. In this example, a thin film layer 812 may be used as an inner liner, which may comprise a lubricious thermoplastic such as HDPE. The thin film layer 812 may be disposed over coils 808 and 814, with the thin film layer 812 extending to the inner lumen between turns of the coils 808 and 814, as shown. Alternatively, the thin film layer 812 may be disposed under coils 808 and 814. In the former instance, the thin film layer 812 may be applied over the coils 808 and 814 using heat and inward pressure as described previously. In the latter instance, the thin film layer 812 may be applied under the coils 808 and 814 using heat and outward pressure. Outer layer 810 comprising, for example, PEBAX or VESTAMID, may be disposed over the thin film layer 812 as shown, or if the thin film layer 812 is disposed under the coils 808 and 814, the outer layer may be disposed over the coils 808 and 814. A reflow process, for example, as described herein, may be used to cause the outer layer 810 to extend into the space between turns of the coils 808 and 814. A thin film tie layer (not shown) may be used to enhance the connection between the lubricious inner layer 812 and the outer layer 810.

As shown in FIG. 8A, as well as FIG. 8B, which is a detailed section view of the box shown in FIG. 8A, the shaft 802 may incorporate tow coil sections, namely distal coil 808 and more proximal coil 814. The two coils 808 and 814 may comprise different materials, different dimensions, and different winding parameters. For example, the distal coil 808 may be more radiopaque than the more proximal coil 814. In this example, the distal coil 808 may comprise a rectangular ribbon (e.g., 0.005"×0.0015") with a tantalum core 809 (approximately 40% by cross sectional area) and a jacket 809 of spring temper MP35N or stainless-steel, and the more proximal coil 814 may comprise a stainless-steel ribbon, both available from Fort Wayne, IN. In addition, the distal coil 808 may have greater spacing between turns than the more proximal coil 814, such that the distal portion of the catheter shaft 802 is more flexible. Laser spot welds, as described previously, may be used to connect the coils 808 and 814 and secure the ends thereof. In addition, the coils 808 and 814 may be coated with a polymer 816 such as polyamide or parylene by vapor deposition to enhance the connection between the coils 808 and 814 to the thin film layer 812. Collectively, these features may provide a thin-walled aspiration catheter 800 with a larger aspiration lumen without increasing the outside profile of the catheter 800.

The constructions, features, and manufacturing techniques described herein may be incorporated, in whole or in part, taken alone or in combination, into a variety of catheters such as the guide, diagnostic, micro, balloon and aspiration catheters, as described herein by way of example, not limitation. The same may be applied to other vascular catheters such as oncology catheters as well as non-vascular catheters such as bronchial catheters.

What is claimed is:

1. A method of making a catheter, comprising:
- cutting a thin film extruded thermoplastic sheet into at least one ribbon;
- forming a first assembly by positioning the ribbon inside a shrink tube and urging the ribbon to assume a tubular shape in which the ribbon defines a ribbon lumen;
- forming a second assembly by loading a lubricious inner tubular member over a mandrel and forming or placing a support structure over an outer surface of the lubricious inner tubular member;
- forming a third assembly by inserting the second assembly into the ribbon lumen defined by the ribbon of the first assembly;
- heating the third assembly to a process temperature, the process temperature being selected such that the shrink tube shrinks and the ribbon reflows to form an encapsulation layer overlaying the support structure and the lubricious inner tubular member, the encapsulation layer being mechanically interlocked with the support structure; and
- removing the shrink tube.

2. The method of making a catheter as in claim 1, further comprising:
- connecting the third assembly to a distal end of a saddle member.

3. The method of making a catheter as in claim 2, further comprising:
- connecting a push rod to a proximal end of the saddle member.

4. The method of claim 1, further comprising positioning a ring member about the shrink tube and moving the ring member in a proximal direction and/or a distal direction along the shrink tube.

5. The method of claim 1 wherein providing the thin film extruded thermoplastic sheet comprises providing a thin film extruded thermoplastic sheet having two or more layers.

6. The method of claim 2 wherein providing the thin film extruded thermoplastic sheet comprises providing a thin film extruded thermoplastic sheet having three or more layers.

7. The method of claim 1 wherein providing the thin film extruded thermoplastic sheet comprises providing a thin film extruded thermoplastic sheet that has a thickness of less than 0.0015".

8. The method of claim 4 wherein providing the thin film extruded thermoplastic sheet comprises providing a thin film extruded thermoplastic sheet that has a thickness of less than 0.0010".

9. The method of claim 6 wherein providing the thin film extruded thermoplastic sheet comprises providing a thin film extruded thermoplastic sheet that has a thickness of less than 0.00075".

10. The method of claim 7 wherein providing the thin film extruded thermoplastic sheet comprises providing a thin film extruded thermoplastic sheet that has a thickness of less than 0.0005".

* * * * *